(12) United States Patent (10) Patent No.: US 9,040,523 B2
Meerpoel et al. (45) Date of Patent: May 26, 2015

(54) ANTIFUNGAL 5,6-DIHYDRO-4H-PYRROLO[1,2-α][1,4]-BENZODIAZEPINES AND 6H-PYRROLO[1,2-α][1,4]BENZODIAZEPINES SUBSTITUTED WITH BENZENE DERIVATIVES

(75) Inventors: Lieven Meerpoel, Turnhoutseweg (BE); Louis Jules Roger Marie Maes, Prinsstraat (BE); Kelly de Wit, Hendrik van Boutersemstraat (BE)

(73) Assignee: JANSSEN PHARMACEUTICA NV, Beerse (BE)

( * ) Notice: Subject to any disclaimer, the term of this patent is extended or adjusted under 35 U.S.C. 154(b) by 68 days.

(21) Appl. No.: 13/989,233

(22) PCT Filed: Nov. 18, 2011

(86) PCT No.: PCT/EP2011/070458
§ 371 (c)(1),
(2), (4) Date: May 23, 2013

(87) PCT Pub. No.: WO2012/069380
PCT Pub. Date: May 31, 2012

(65) Prior Publication Data
US 2013/0274250 A1    Oct. 17, 2013

(30) Foreign Application Priority Data
Nov. 24, 2010 (EP) .................................. 10192321

(51) Int. Cl.
*A61K 31/5517* (2006.01)
*C07D 487/04* (2006.01)
(52) U.S. Cl.
CPC ..................................... *C07D 487/04* (2013.01)
(58) Field of Classification Search
CPC .......................... A61K 31/5517; C07D 487/04
USPC .......................................... 514/220; 540/561
See application file for complete search history.

(56) References Cited

FOREIGN PATENT DOCUMENTS

WO    WO 02/34752 A1    5/2002

OTHER PUBLICATIONS

Butin, A., et al., "Furan Ring Opening-Pyrrole Ring Closure: A New Synthetic Route to Aryl(heteroaryl)-annylated Pyrrolo[1,2-α][1,4]Diazepines", Organic & Biomedical Chemistry, vol. 8, pp. 3316-3327 (2010).
Cheeseman, G., et al., "Synthesis of 5,6-Dihydro-4H-pyrrolo[1,3-α][1,4]Benzodiazepines", J. Heterocyclic Chemistry, vol. 16, pp. 241-144, 1979.
Cheeseman, G., et al, "Further Cyclisation Reactions of 1-Ayrlpyrroles", J. Chemical Society, pp. 2732-2734 (1971).
Meerpoel, L, et al, {"Pyrrolo[1,2-α][1,4]Benzodiazpine: A Novel Class of Non-Azole Anti-Dermatophyte Anti-Fungal Agents", Bioorganic & Medicinal Chemistry Letters, vol. 15, pp. 3453-3458 (2005).
Raines, S., et al., "Mannich Reactions. Synthesis of 4,5-Dihydropyrrolo[1,2-α]Quinoxalines, 2,3,4,5-Tetrahydro-1H-prrolo] 1,2-α][1.4] Diazepines and 5,6-Dihydro-4H-prrolo[1,2-α] [1.4] Benzodiazepines", J. Heterocyclic Chemistry, vol. 13, pp. 711-716 (1976).
Trinka, P., et al., "A Convenient Synthesis of Ethyl (2-Amin-5,6-dichlorobenzyl)glycinate", J. Prakt. Chem., vol. 338, pp. 675-678 (1996).
European Search Report for Application No. EP10192321 completed Mar. 2, 2011.
International Search Report for Application No. PCT/EP2011/070458 dated May 23, 2013.
International Search Report for Application No. PCTE2011/073215 dated Jun. 25, 2013.
European Search Report for Application No. EP10196201 completed Mar. 4, 2011.
European Search Report completed Aug. 8, 2011 for Application No. EP11164960.
International Search Report dated Nov. 5, 2013 for Application No. PCT/EP2012/058142.

*Primary Examiner* — Brenda Coleman
(74) *Attorney, Agent, or Firm* — Thomas J. Dodd

(57) ABSTRACT

The present invention is concerned with novel antifungal 5,6-dihydro-4H-pyrrolo-[1,2-a][1,4]benzodiazepines and 6H-pyrrolo[1,2-a][1,4]benzodiazepines of Formula (I)

(I)

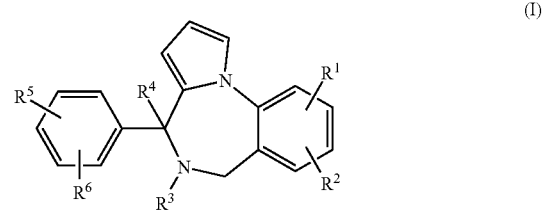

wherein $R^1$, $R^2$, $R^3$, $R^4$, $R^5$ and $R^6$ have the meaning defined in the claims. The compounds according to the present invention are active mainly against dermatophytes and systemic fungal infections. The invention further relates to processes for preparing such novel compounds, pharmaceutical compositions comprising said compounds as an active ingredient as well as the use of said compounds as a medicament.

12 Claims, No Drawings

ANTIFUNGAL 5,6-DIHYDRO-4H-PYRROLO[1,2-α][1,4]-BENZODIAZEPINES AND 6H-PYRROLO[1,2-α][1,4]BENZODIAZEPINES SUBSTITUTED WITH BENZENE DERIVATIVES

CROSS-REFERENCE TO RELATED APPLICATIONS

The present application claims the benefits of the filing of Application Nos. EP 10192321.7 filed Nov. 24, 2010, and PCT/EP2011/070458 (WO2012/069380) filed Nov. 18, 2011. The complete disclosures of the aforementioned related patent applications are hereby incorporated herein by reference for all purposes.

FIELD OF THE INVENTION

The present invention is concerned with novel antifungal 5,6-dihydro-4H-pyrrolo-[1,2-a][1,4]benzodiazepines and 6H-pyrrolo[1,2-a][1,4]benzodiazepines, both substituted with benzene derivatives, active mainly against dermatophytes and systemic fungal infections. The invention further relates to processes for preparing such novel compounds, pharmaceutical compositions comprising said compounds as an active ingredient as well as the use of said compounds as a medicament.

BACKGROUND OF THE INVENTION

Dermatophyte is a common label for a group of 3 types of fungi that commonly causes skin disease in animals and humans. These anamorphic (asexual or imperfect fungi) genera are: *Microsporum, Epidermophyton* and *Trichophyton*. There are about 40 species in these 3 genera.

Dermatophytes cause infections of the skin, hair and nails due to their ability to obtain nutrients from keratinized material. The organisms colonize the keratin tissues and inflammation is caused by host response to metabolic by-products. They are usually restricted to the cornified layer of the epidermis because of their inability to penetrate viable tissue of an immunocompetent host. However, occasionally the organisms do invade subcutaneous tissues, resulting in kerion development. Invasion does elicit a host response ranging from mild to severe. Acid proteinases, elastase, keratinases, and other proteinases reportedly act as virulence factors.

Systemic fungal infections (SFI) are life-threatening conditions that most commonly affect patients with reduced immunity often resulting from therapeutic interventions to treat malignant diseases. The number of SFI's in modern hospitals keeps increasing, and the number of different fungi that have been involved in SFI is large and still growing. Despite many cases of invasive candidiasis and aspergillosis there has been an increased incidence of infections due to other molds like *Scedosporium apiospermum, Fusarium* spp., and *Zygomycetes, Rhizopus* and *Mucor* spp. Effective therapeutic agents treating all these infections very well therefore need to have very broad spectrum of activity. In the past few decades itraconazole, fluconazole, ketoconazole, and intravenous or liposomal amphotericin B have been used in SFI, and all of these agents have their limitations with regard to spectrum, safety or ease of administration. More recently a third generation of azoles have been investigated and introduced to the market, improving the treatment options in intensive care units. Voriconazole (Vfend™) and posaconazole (Noxafil™) show much improvement of treatment towards life threatening invasive SFI such as candidiasis, aspergillosis, and infections due to *Fusarium* species at clinical relevant dosages. Moreover posaconazole shows efficacy against infections caused by the emerging *Zygomycetes* spp. Echinocandins, such as anidulafungin, caspofungin, and micafungin, which are non-competitive inhibitors of 1,3-β-glucan synthesis in fungal cell walls, display high efficacy against *Candida* spp. and *Aspergillus* spp., but no activity against *Cryptococcus, Fusarium*, or *Zygomycetes* spp. Of all antimycotic agents, azoles still represent a unique class of compounds displaying the broadest antifungal spectrum via inhibition of 14-α-demethylase, an enzyme being essential for ergosterol biosynthesis in fungi.

Onychomycosis is the most common disease of the nails and constitutes about a half of all nail abnormalities. The prevalence of onychomycosis is about 6-8% in the adult population. The causative pathogens of onychomycosis include dermatophytes, *Candida*, and non-dermatophytic moulds. Dermatophytes are the fungi most commonly responsible for onychomycosis in the temperate western countries; meanwhile, *Candida* and non-dermatophytic moulds are more frequently involved in the tropics and subtropics. *Trichophyton rubrum* is the most common dermatophyte involved in onychomycosis. Other dermatophytes that may be involved are *Trichophyton interdigitale, Epidermophyton floccosum, Trichophyton violaceum, Microsporum gypseum, Trichophyton tonsurans, Trichophyton soudanense* and *Trichophyton verrucosum*. Other causative pathogens include *Candida* and non-dermatophytic moulds, in particular members of the mould generation *Scytalidium* (also *Neoscytalidium*), *Scopulariopsis*, and *Aspergillus*.

5,6-Dihydro-4H-pyrrolo[1,2-a][1,4]benzodiazepines have been described in J. Chem. Soc. (C), 2732-2734 (1971); J. Heterocyclic Chem., 13, 711-716 (1976); and J. Heterocyclic Chem., 16, 241-244 (1979). The compounds disclosed in these references all have a different substitution on the phenyl moiety in the 4-position and moreover no biological activities were reported in any of these references.

WO02/34752 describes 4-substituted 5,6-dihydro-4H-pyrrolo[1,2-a][1,4]benzo-diazepines as a new class of antifungal compounds. However, WO02/34752 does not disclose the present substitution pattern on the phenyl moiety in the 4-position.

The PhD thesis of De Wit K. describes the implementation of an in vitro and in vivo mycological evaluation platform and activity profiling of antifungal pyrrolobenzodiazepines (PhD Thesis; University of Antwerp, Belgium; Faculty of Pharmaceutical, Biomedical and Veterinary Sciences; Department of Biomedical Sciences; 2011; 220 p.).

The antifungal compounds of the present invention or part of the compounds of the present invention are structurally different and may have improved metabolic stability properties, improved PK (pharmacokinetic) properties, improved plasma binding, reduced hERG channel inhibition, reduced cytochrome P450 liabilities, or improved bioavailability compared with compounds disclosed in the prior art. Preferably said compounds have a broad antifungal spectrum, and maintain adequately hight therapeutic efficacy and adequately low toxicity or other side effects.

It is accordingly an object of the present invention to provide novel compounds with antifungal activity to overcome or ameliorate at least one of the disadvantages of the prior art, or to provide useful alternative compounds.

SUMMARY OF THE INVENTION

It has been found that the compounds of the present invention are useful as antifungal compounds.

The present invention concerns novel compounds of Formula (I):

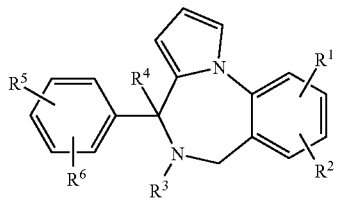

and stereoisomeric forms thereof, wherein $R^1$ is hydrogen, halo, $C_{1-4}$alkyl or $C_{1-4}$alkyloxy;

$R^2$ is hydrogen or halo;

$R^3$ and $R^4$ are hydrogen;

or $R^3$ and $R^4$ taken together form a bond;

$R^5$ is $C_{1-4}$alkylcarbonyl, $C_{1-4}$alkylsulphonyl, $C_{1-4}$alkylsulphinyl, or $C_{1-4}$alkyl substituted with one hydroxyl moiety;

$R^6$ is hydrogen or halo;

and the pharmaceutically acceptable addition salts, and the solvates thereof.

The present invention also concerns methods for the preparation of compounds of Formula (I) and pharmaceutical compositions comprising them.

The present compounds are useful agents for combating fungi in vivo.

The novel compounds described in the present invention may be useful in the treatment or prevention of infections caused by dermatophytes, systemic fungal infections and onychomycosis.

The novel compounds described in the present invention may be active against a wide variety of fungi, such as *Candida* spp., e.g. *Candida albicans, Candida glabrata, Candida krusei; Candida parapsilosis, Candida kefyr, Candida tropicalis; Aspergillus* spp., e.g. *Aspergillus fumigatus, Aspergillus niger, Aspergillus flavus; Cryptococcus neoformans; Sporothrix schenckii; Epidermophyton floccosum; Microsporum* spp., e.g. *Microsporum canis, Microsporum gypseum; Trichophyton* spp., e.g. *Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium* spp., e.g. *Fusarium solani, Fusarium oxysporum, Fusarium proliferatum, Fusarium verticillioides; Rhizomucor* spp., e.g. *Rhizomucor miehei, Rhizomucor pusillus; Mucor circinelloides; Rhizopus* spp., e.g. *Rhizopus oryzae, Rhizopus microspores; Malassezia furfur; Acremonium* spp.; *Paecilomyces; Scopulariopsis; Arthrographis* spp.; *Scytalidium; Scedosporium* spp., e.g. *Scedosporium apiospermum, Scedosporium prolificans; Trichoderma* spp.; *Penicillium* spp.; *Penicillium marneffei; Blastoschizomyces*.

In view of the aforementioned pharmacology of the present compounds, it follows that they are suitable for use as a medicament.

The invention also relates to a compound according to the general Formula (I), the stereoisomeric forms thereof and the pharmaceutically acceptable addition salts and the solvates thereof, for use in the treatment or prevention of fungal infections.

One advantage of the compounds or a part of the compounds of the present invention may lie in their enhanced bioavailability, improved metabolic stability properties, improved PK properties, reduced hERG channel inhibition, or reduced cytochrome P450 liabilities compared with the compounds disclosed in the prior art.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

The term "halo" or "halogen" as a group or part of a group is generic for fluoro, chloro, bromo, iodo unless otherwise is indicated or is clear from the context.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl includes all linear, or branched alkyl groups with between 1 and 4 carbon atoms, and thus includes such as for example methyl, ethyl, n-propyl, i-propyl, 2-methyl-ethyl, butyl and its isomers (e.g. n-butyl, isobutyl and tert-butyl), and the like.

The term "$C_{1-4}$alkyloxy" as a group or part of a group refers to a radical having the Formula $-OR^a$ wherein $R^a$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

The term "$C_{1-4}$alkylsulfonyl" refers to a straight chain or branched chain alkylsulfonyl group having from 1 to 4 carbon atoms, such as methylsulfonyl, ethylsulfonyl, propylsulfonyl, isopropylsulfonyl, butylsulfonyl, isobutylsulfonyl, sec-butylsulfonyl, tert-butylsulfonyl and the like.

The term "$C_{1-4}$alkylcarbonyl" refers to a straight chain or branched chain alkylcarbonyl group having from 1 to 5 carbon atoms, such as methylcarbonyl, ethylcarbonyl, propylcarbonyl, isopropylcarbonyl, butylcarbonyl, isobutylcarbonyl, sec-butylcarbonyl, tert-butylcarbonyl and the like.

The chemical names of the compounds of the present invention were generated according to the nomenclature rules agreed upon by the Chemical Abstracts Service, using Advanced Chemical Development, Inc., nomenclature software (ACD/Name product version 10.01; Build 15494, 1 Dec. 2006).

In case of tautomeric forms, it should be clear that the other non-depicted tautomeric form is also included within the scope of the present invention.

The atoms in the tricyclic system are numbered as shown in the following formula (Q):

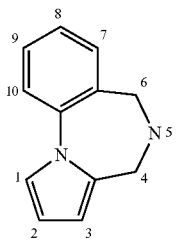

(Q)

It will be appreciated that some of the compounds of Formula (I) and their pharmaceutically acceptable addition salts and solvates may contain one or more centers of chirality and exist as stereoisomeric forms.

As used in the description, whenever the term "compound(s) of formula (I)" is used, it is meant to include the stereoisomeric forms thereof, and the pharmaceutically acceptable addition salts, and the solvates thereof.

The terms "stereoisomers", "stereoisomeric forms" or "stereochemically isomeric forms" hereinbefore or hereinafter are used interchangeably.

The term "stereoisomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms.

The definition of "compound of formula (I)" inherently includes all stereoisomers of the compound of formula (I) either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereoisomeric forms of the compounds of Formula (I) are embraced within the scope of this invention. Therefore, the invention includes enantiomers, diastereomers, racemates, E isomers, Z isomers, cis isomers, trans isomers and mixtures thereof, whenever chemically possible.

The absolute configuration is specified according to the Cahn-Ingold-Prelog system.

The configuration at an asymmetric atom is specified by either R or S. Resolved compounds whose absolute configuration is not known can be designated by (+) or (−) depending on the direction in which they rotate plane polarized light.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s). Thus, when a compound of the present invention is for instance specified as (R), this means that the compound is substantially free of the (S) isomer; when a compound of the present invention is for instance specified as E, this means that the compound is substantially free of the Z isomer; when a compound of the present invention is for instance specified as cis, this means that the compound is substantially free of the trans isomer.

Some of the compounds of formula (I) may also exist in their tautomeric form. Such forms although not explicitly indicated in the above formula are intended to be included within the scope of the present invention.

The compounds of formula (I) have been drawn herein in a single tautomeric form, the different tautomers are equivalent to each other and all possible tautomeric forms are included within the scope of the invention.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as the salts thereof. Examples of such forms are e.g. hydrates, alcoholates and the like.

The compounds of Formula (I) as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, a compound according to the invention is inherently intended to comprise all isotopic combinations of its chemical elements. In the framework of this application, a chemical element, in particular when mentioned in relation to a compound according to Formula (I), comprises all isotopes and isotopic mixtures of this element. For example, when hydrogen is mentioned, it is understood to refer to $^1H$, $^2H$, $^3H$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to Formula (I), or a pharmaceutically acceptable salt thereof, which contains at least one radioactive atom. For example, a compound can be labelled with positron or with gamma emitting radioactive isotopes. For radioligand-binding techniques, the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$.

As used in the specification and the appended claims, the singular forms "a", "an," and "the" also include plural referents unless the context clearly dictates otherwise. By way of example, "a compound" means one compound or more than one compound.

The terms described above and others used in the specification are well understood to those in the art.

Preferred features of the compounds of this invention are now set forth.

The present invention concerns novel compounds of Formula (I):

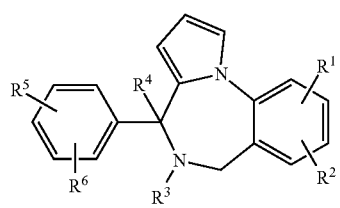

(I)

and stereoisomeric forms thereof, wherein
$R^1$ is hydrogen, halo, $C_{1-4}$alkyl or $C_{1-4}$alkyloxy;
$R^2$ is hydrogen or halo;
$R^3$ and $R^4$ are hydrogen;
or $R^3$ and $R^4$ taken together form a bond;
$R^5$ is $C_{1-4}$alkylcarbonyl, $C_{1-4}$alkylsulphonyl, $C_{1-4}$alkylsulphinyl, or $C_{1-4}$alkyl substituted with one hydroxyl moiety;
$R^6$ is hydrogen or halo;
and the pharmaceutically acceptable addition salts, and the solvates thereof.

In an embodiment, the invention relates to compounds of Formula (I) and stereoisomeric forms thereof, wherein
$R^1$ is hydrogen, halo, $C_{1-4}$alkyl or $C_{1-4}$alkyloxy;
$R^2$ is hydrogen or halo;
$R^3$ and $R^4$ are hydrogen;
or $R^3$ and $R^4$ taken together form a bond;
$R^5$ is $C_{1-4}$alkylcarbonyl, $C_{1-4}$alkylsulphonyl, or $C_{1-4}$alkyl substituted with one hydroxyl moiety;
$R^6$ is hydrogen or halo;
and the pharmaceutically acceptable addition salts, and the solvates thereof.

In an embodiment, the invention relates to compounds of Formula (I) and stereoisomeric forms thereof, wherein
$R^1$ is hydrogen, halo, $C_{1-4}$alkyl or $C_{1-4}$alkyloxy; in particular $R^1$ is halo;
$R^2$ is hydrogen or halo;
$R^3$ and $R^4$ are hydrogen;
or $R^3$ and $R^4$ taken together form a bond;
$R^5$ is $C_{1-4}$alkylcarbonyl or $C_{1-4}$alkylsulphonyl; in particular $C_{1-4}$alkylcarbonyl;
$R^6$ is hydrogen or halo;
and the pharmaceutically acceptable addition salts, and the solvates thereof.

In an embodiment, the invention relates to compounds of Formula (I) and stereoisomeric forms thereof, wherein
$R^1$ is hydrogen, halo, $C_{1-4}$alkyl or $C_{1-4}$alkyloxy; in particular $R^1$ is halo;
$R^2$ is hydrogen or halo;
$R^3$ and $R^4$ are hydrogen;
or $R^3$ and $R^4$ taken together form a bond;
$R^5$ is $C_{1-4}$alkylcarbonyl, or $C_{1-4}$alkyl substituted with one hydroxyl moiety;
$R^6$ is hydrogen or halo;
and the pharmaceutically acceptable addition salts, and the solvates thereof.

In an embodiment, the invention relates to compounds of Formula (I) and stereoisomeric forms thereof, wherein
$R^1$ is hydrogen, halo, $C_{1-4}$alkyl or $C_{1-4}$alkyloxy; in particular $R^1$ is halo;
$R^2$ is hydrogen or halo;
$R^3$ and $R^4$ are hydrogen;
$R^5$ is $C_{1-4}$alkylcarbonyl, $C_{1-4}$alkylsulphinyl, $C_{1-4}$alkylsulphonyl, or $C_{1-4}$alkyl substituted with one hydroxyl moiety; in particular $R^5$ is $C_{1-4}$alkylcarbonyl, $C_{1-4}$alkylsulphonyl, or $C_{1-4}$alkyl substituted with one hydroxyl moiety; more in particular $R^5$ is $C_{1-4}$alkylcarbonyl;
$R^6$ is hydrogen or halo;
and the pharmaceutically acceptable addition salts, and the solvates thereof.

In an embodiment, the invention relates to compounds of Formula (I) and stereoisomeric forms thereof, wherein
$R^1$ is hydrogen, halo, $C_{1-4}$alkyl or $C_{1-4}$alkyloxy; in particular $R^1$ is halo;
$R^2$ is hydrogen or halo;
$R^3$ and $R^4$ taken together form a bond;
$R^5$ is $C_{1-4}$alkylcarbonyl, $C_{1-4}$alkylsulphinyl, $C_{1-4}$alkylsulphonyl, or $C_{1-4}$alkyl substituted with one hydroxyl moiety; in particular $R^5$ is $C_{1-4}$alkylcarbonyl, $C_{1-4}$alkylsulphonyl, or $C_{1-4}$alkyl substituted with one hydroxyl moiety; more in particular $R^5$ is $C_{1-4}$alkylcarbonyl;
$R^6$ is hydrogen or halo; in particular $R^6$ is hydrogen;

and the pharmaceutically acceptable addition salts, and the solvates thereof.

In an embodiment, the invention relates to compounds of Formula (I) and stereoisomeric forms thereof, wherein
$R^1$ is halo;
$R^2$ is hydrogen or halo;
$R^3$ and $R^4$ taken together form a bond;
$R^5$ is $C_{1-4}$alkylcarbonyl, $C_{1-4}$alkylsulphonyl, or $C_{1-4}$alkyl substituted with one hydroxyl moiety; in particular $R^5$ is $C_{1-4}$alkylcarbonyl or $C_{1-4}$alkylsulphonyl;
$R^6$ is hydrogen or halo;
and the pharmaceutically acceptable addition salts, and the solvates thereof.

In an embodiment, the invention relates to compounds of Formula (I) and stereoisomeric forms thereof, wherein
$R^1$ is halo;
$R^2$ is hydrogen or halo;
$R^3$ and $R^4$ are hydrogen;
or $R^3$ and $R^4$ taken together form a bond;
$R^5$ is $C_{1-4}$alkylcarbonyl, $C_{1-4}$alkylsulphinyl, $C_{1-4}$alkylsulphonyl, or $C_{1-4}$alkyl substituted with one hydroxyl moiety; in particular $R^5$ is $C_{1-4}$alkylcarbonyl, $C_{1-4}$alkylsulphonyl, or $C_{1-4}$alkyl substituted with one hydroxyl moiety;
$R^6$ is hydrogen or halo;
and the pharmaceutically acceptable addition salts, and the solvates thereof.

In an embodiment, the invention relates to compounds of Formula (I) and stereoisomeric forms thereof, wherein
$R^1$ is halo;
$R^2$ is hydrogen or halo;
$R^3$ and $R^4$ are hydrogen;
or $R^3$ and $R^4$ taken together form a bond;
$R^5$ is $C_{1-4}$alkylcarbonyl;
$R^6$ is hydrogen or halo;
and the pharmaceutically acceptable addition salts, and the solvates thereof.

In an embodiment, the invention relates to compounds of Formula (I) and stereoisomeric forms thereof, wherein
$R^1$ is halo; in particular chloro or fluoro; more in particular chloro;
$R^2$ is hydrogen or halo; in particular hydrogen, chloro of fluoro;
$R^3$ and $R^4$ are hydrogen;
or $R^3$ and $R^4$ taken together form a bond;
$R^5$ is $C_{1-4}$alkylcarbonyl, $C_{1-4}$alkylsulphonyl, or $C_{1-4}$alkyl substituted with one hydroxyl moiety; in particular methylcarbonyl, methylsulphonyl or 1-hydroxyethyl;
$R^6$ is hydrogen or halo; in particular hydrogen or fluoro; more in particular hydrogen; and the pharmaceutically acceptable addition salts, and the solvates thereof.

An embodiment of the present invention relates to those compounds of formula (I) or any subgroup thereof as mentioned in any of the other embodiments wherein $R^1$ is halo, $C_{1-4}$alkyl or $C_{1-4}$alkyloxy; and wherein $R^2$ is halo; in particular wherein $R^1$ and $R^2$ both are halo.

An embodiment of the present invention relates to those compounds of formula (I) or any subgroup thereof as mentioned in any of the other embodiments wherein at least one of $R^1$ and $R^2$ is other than hydrogen.

An embodiment of the present invention relates to those compounds of formula (I) or any subgroup thereof as mentioned in any of the other embodiments wherein $R^1$ is halo.

An embodiment of the present invention relates to those compounds of formula (I) or any subgroup thereof as mentioned in any of the other embodiments wherein $R^2$ is halo.

An embodiment of the present invention relates to those compounds of formula (I) or any subgroup thereof as mentioned in any of the other embodiments wherein $R^3$ and $R^4$ taken together form a bond.

An embodiment of the present invention relates to those compounds of formula (I) or any subgroup thereof as mentioned in any of the other embodiments wherein $R^5$ is $C_{1-4}$alkylcarbonyl; $C_{1-4}$alkylsulphonyl; or $C_{1-4}$alkyl substituted with one hydroxyl moiety.

An embodiment of the present invention relates to those compounds of formula (I) or any subgroup thereof as mentioned in any of the other embodiments wherein $R^5$ is $C_{1-4}$alkylcarbonyl; in particular methylcarbonyl.

An embodiment of the present invention relates to those compounds of formula (I) or any subgroup thereof as mentioned in any of the other embodiments wherein $R^5$ is $C_{1-4}$alkylsulphonyl.

An embodiment of the present invention relates to those compounds of formula (I) or any subgroup thereof as mentioned in any of the other embodiments wherein $R^5$ is methylcarbonyl, methylsulphonyl or 1-hydroxyethyl;

An embodiment of the present invention relates to those compounds of formula (I) or any subgroup thereof as mentioned in any of the other embodiments wherein $R^6$ is halo.

An embodiment of the present invention relates to those compounds of formula (I) or any subgroup thereof as mentioned in any of the other embodiments wherein $R^6$ is hydrogen.

An interesting group of compounds concerns novel compounds of Formula (I), having one or more of the Formulae selected from (I-x) and (I-y) and stereoisomeric forms thereof

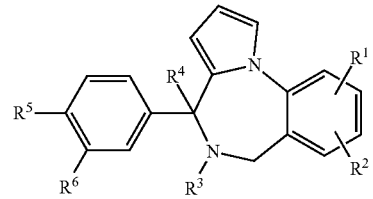

(I-x)

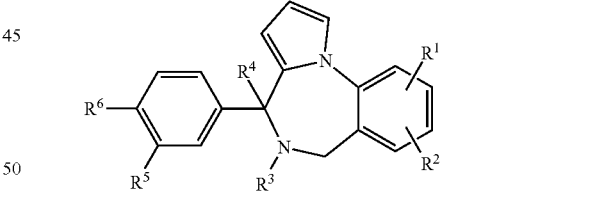

(I-y)

wherein all the substituents have the same meaning as defined in any of the embodiments hereinbefore,
and the pharmaceutically acceptable addition salts and the solvates thereof.

An embodiment of the present invention relates to those compounds of formula (I) or any subgroup thereof, having Formula (I-x).

An embodiment of the present invention relates to those compounds of formula (I) or any subgroup thereof, having Formula (I-y).

In an embodiment, the invention relates to compounds of Formula (I-x) and (I-y) and stereoisomeric forms thereof, wherein
$R^1$ is halo; in particular chloro or fluoro; more in particular chloro;

$R^2$ is hydrogen or halo; in particular hydrogen, chloro of fluoro;
$R^3$ and $R^4$ are hydrogen;
or $R^3$ and $R^4$ taken together form a bond;
$R^5$ is $C_{1-4}$alkylcarbonyl, $C_{1-4}$alkylsulphonyl, $C_{1-4}$alkylsulphinyl, or $C_{1-4}$alkyl substituted with one hydroxyl moiety; in particular $R^5$ is $C_{1-4}$alkylcarbonyl, $C_{1-4}$alkylsulphonyl, or $C_{1-4}$alkyl substituted with one hydroxyl moiety; more in particular methylcarbonyl, methylsulphonyl or 1-hydroxyethyl;
$R^6$ is hydrogen or halo; in particular hydrogen or fluoro; more in particular hydrogen;
and the pharmaceutically acceptable addition salts, and the solvates thereof.

In an embodiment, the invention relates to compounds of Formula (I-x) and stereoisomeric forms thereof, wherein
$R^1$ is halo; in particular chloro or fluoro; more in particular chloro;
$R^2$ is hydrogen or halo; in particular hydrogen, chloro of fluoro;
$R^3$ and $R^4$ are hydrogen;
or $R^3$ and $R^4$ taken together form a bond;
$R^5$ is $C_{1-4}$alkylcarbonyl, $C_{1-4}$alkylsulphonyl, $C_{1-4}$alkylsulphinyl, or $C_{1-4}$alkyl substituted with one hydroxyl moiety; in particular $R^5$ is $C_{1-4}$alkylcarbonyl, $C_{1-4}$alkylsulphonyl, or $C_{1-4}$alkyl substituted with one hydroxyl moiety; more in particular methylcarbonyl, methylsulphonyl or 1-hydroxyethyl;
$R^6$ is hydrogen or halo; in particular hydrogen or fluoro; more in particular hydrogen;
and the pharmaceutically acceptable addition salts, and the solvates thereof.

In an embodiment, the invention relates to compounds of Formula (I-y) and stereoisomeric forms thereof, wherein
$R^1$ is halo; in particular chloro or fluoro; more in particular chloro;
$R^2$ is hydrogen or halo; in particular hydrogen, chloro of fluoro;
$R^3$ and $R^4$ are hydrogen;
or $R^3$ and $R^4$ taken together form a bond;
$R^5$ is $C_{1-4}$alkylcarbonyl, $C_{1-4}$alkylsulphonyl, $C_{1-4}$alkylsulphinyl, or $C_{1-4}$alkyl substituted with one hydroxyl moiety; in particular $R^5$ is $C_{1-4}$alkylcarbonyl, $C_{1-4}$alkylsulphonyl, or $C_{1-4}$alkyl substituted with one hydroxyl moiety; more in particular methylcarbonyl, methylsulphonyl or 1-hydroxyethyl;
$R^6$ is hydrogen or halo; in particular hydrogen or fluoro; more in particular hydrogen;
and the pharmaceutically acceptable addition salts, and the solvates thereof.

An embodiment of the present invention relates to those compounds of formula (I) or any subgroup thereof as mentioned in any of the other embodiments wherein $R^3$ and $R^4$ are always taken together form a bond.

In a next embodiment the compound of Formula (I) is selected from the group consisting of:
1-[4-(7-chloro-5,6-dihydro-4H-pyrrolo[1,2-a][1,4]benzodiazepin-4-yl)phenyl]-ethanone .HCl,
1-[4-(7-chloro-5,6-dihydro-4H-pyrrolo[1,2-a][1,4]benzodiazepin-4-yl)phenyl]-ethanone .HBr,
1-[4-(7-chloro-5,6-dihydro-4H-pyrrolo[1,2-a][1,4]benzodiazepin-4-yl)phenyl]-ethanone,
1-[4-(7-chloro-6H-pyrrolo[1,2-a][1,4]benzodiazepin-4-yl)phenyl]-ethanone,
1-[4-(7,8-dichloro-5,6-dihydro-4H-pyrrolo[1,2-a][1,4]benzodiazepin-4-yl)phenyl]-ethanone .HCl,
1-[4-(7,8-dichloro-5,6-dihydro-4H-pyrrolo[1,2-a][1,4]benzodiazepin-4-yl)phenyl]-ethanone,
1-[4-(8,10-dichloro-5,6-dihydro-4H-pyrrolo[1,2-a][1,4]benzodiazepin-4-yl)phenyl]-ethanone .HCl,
1-[4-(8,10-dichloro-5,6-dihydro-4H-pyrrolo[1,2-a][1,4]benzodiazepin-4-yl)phenyl]-ethanone,
1-[4-(8,10-dichloro-6H-pyrrolo[1,2-a][1,4]benzodiazepin-4-yl)phenyl]-ethanone,
4-(7-chloro-5,6-dihydro-4H-pyrrolo[1,2-a][1,4]benzodiazepin-4-yl)-alpha-methyl-benzenemethanol,
1-[4-(7,8-dichloro-6H-pyrrolo[1,2-a][1,4]benzodiazepin-4-yl)phenyl]-ethanone,
1-[4-(7,8-dichloro-6H-pyrrolo[1,2-a][1,4]benzodiazepin-4-yl)phenyl]-ethanone .HCl,
4-(7,8-dichloro-5,6-dihydro-4H-pyrrolo[1,2-a][1,4]benzodiazepin-4-yl)-alpha-methyl-benzenemethanol .HCl,
4-(7,8-dichloro-5,6-dihydro-4H-pyrrolo[1,2-a][1,4]benzodiazepin-4-yl)-alpha-methyl-benzenemethanol,
4-(8,10-dichloro-5,6-dihydro-4H-pyrrolo[1,2-a][1,4]benzodiazepin-4-yl)-alpha-methyl-benzenemethanol .HCl,
4-(8,10-dichloro-5,6-dihydro-4H-pyrrolo[1,2-a][1,4]benzodiazepin-4-yl)-alpha-methyl-benzenemethanol,
1-[3-(7-chloro-5,6-dihydro-4H-pyrrolo[1,2-a][1,4]benzodiazepin-4-yl)phenyl]-ethanone,
1-[4-(7,9-dichloro-5,6-dihydro-4H-pyrrolo[1,2-a][1,4]benzodiazepin-4-yl)phenyl]-ethanone .HCl,
1-[4-(7,9-dichloro-5,6-dihydro-4H-pyrrolo[1,2-a][1,4]benzodiazepin-4-yl)phenyl]-ethanone,
1-[3-(7,9-dichloro-5,6-dihydro-4H-pyrrolo[1,2-a][1,4]benzodiazepin-4-yl)phenyl]-ethanone .HCl,
1-[3-(7,9-dichloro-5,6-dihydro-4H-pyrrolo[1,2-a][1,4]benzodiazepin-4-yl)phenyl]-ethanone,
1-[4-(7,9-dichloro-6H-pyrrolo[1,2-a][1,4]benzodiazepin-4-yl)phenyl]-ethanone,
1-[3-(7-chloro-6H-pyrrolo[1,2-a][1,4]benzodiazepin-4-yl)phenyl]-ethanone,
1-[4-(7,10-dichloro-6H-pyrrolo[1,2-a][1,4]benzodiazepin-4-yl)phenyl]-ethanone,
7-chloro-4-[3-(methylsulfonyl)phenyl 6H-pyrrolo[1,2-a][1,4]benzodiazepine,]-7,9-dichloro-4-[3-(methylsulfonyl)phenyl]-6H-pyrrolo[1,2-a][1,4]benzodiazepine,
7-fluoro-4-[4-(methylsulfonyl)phenyl]-6H-pyrrolo[1,2-a][1,4]benzodiazepine,
7-chloro-4-[4-(methylsulfonyl)phenyl]-6H-pyrrolo[1,2-a][1,4]benzodiazepine,
1-[5-(7,9-dichloro-5,6-dihydro-4H-pyrrolo[1,2-a][1,4]benzodiazepin-4-yl)-2-fluorophenyl]-ethanone,
7,9-dichloro-4-[4-(methylsulfonyl)phenyl]-6H-pyrrolo[1,2-a][1,4]benzodiazepine,
1-[4-(9-chloro-5,6-dihydro-4H-pyrrolo[1,2-a][1,4]benzodiazepin-4-yl)phenyl]-ethanone,
1-[5-(7-chloro-5,6-dihydro-4H-pyrrolo[1,2-a][1,4]benzodiazepin-4-yl)-2-fluorophenyl]-ethanone .HCl,
1-[5-(7-chloro-5,6-dihydro-4H-pyrrolo[1,2-a][1,4]benzodiazepin-4-yl)-2-fluorophenyl]-ethanone,
1-[5-(7,9-dichloro-6H-pyrrolo[1,2-a][1,4]benzodiazepin-4-yl)-2-fluorophenyl]-ethanone,
1-[4-(10-chloro-6H-pyrrolo[1,2-a][1,4]benzodiazepin-4-yl)phenyl]-ethanone,
1-[5-(7-chloro-6H-pyrrolo[1,2-a][1,4]benzodiazepin-4-yl)-2-fluorophenyl]-ethanone,
1-[4-(9-chloro-6H-pyrrolo[1,2-a][1,4]benzodiazepin-4-yl)phenyl]-ethanone,
1-[4-(7,9-difluoro-6H-pyrrolo[1,2-a][1,4]benzodiazepin-4-yl)phenyl]-ethanone,
1-[4-(7-fluoro-6H-pyrrolo[1,2-a][1,4]benzodiazepin-4-yl)phenyl]-ethanone, 4-(7,9-dichloro-5,6-dihydro-4H-pyrrolo[1,2-a][1,4]benzodiazepin-4-yl)-benzeneethanol .HCl,
4-(7,9-dichloro-5,6-dihydro-4H-pyrrolo[1,2-a][1,4]benzodiazepin-4-yl)-benzeneethanol,
4-(7-chloro-5,6-dihydro-4H-pyrrolo[1,2-a][1,4]benzodiazepin-4-yl)-benzeneethanol .HCl,
4-(7-chloro-5,6-dihydro-4H-pyrrolo[1,2-a][1,4]benzodiazepin-4-yl)-benzeneethanol,
4-(8,10-dichloro-5,6-dihydro-4H-pyrrolo[1,2-a][1,4]benzodiazepin-4-yl)-benzeneethanol .HCl,
4-(8,10-dichloro-5,6-dihydro-4H-pyrrolo[1,2-a][1,4]benzodiazepin-4-yl)-benzeneethanol,
4-(7,8-dichloro-5,6-dihydro-4H-pyrrolo[1,2-a][1,4]benzodiazepin-4-yl)-benzeneethanol .HCl,
4-(7,8-dichloro-5,6-dihydro-4H-pyrrolo[1,2-a][1,4]benzodiazepin-4-yl)-benzeneethanol,
4-(7,10-dichloro-5,6-dihydro-4H-pyrrolo[1,2-a][1,4]benzodiazepin-4-yl)-benzeneethanol .HCl,
4-(7,10-dichloro-5,6-dihydro-4H-pyrrolo[1,2-a][1,4]benzodiazepin-4-yl)-benzeneethanol,
4-(9-chloro-5,6-dihydro-4H-pyrrolo[1,2-a][1,4]benzodiazepin-4-yl)-benzeneethanol,
1-[4-(7-fluoro-5,6-dihydro-4H-pyrrolo[1,2-a][1,4]benzodiazepin-4-yl)phenyl]-ethanone .HCl,
1-[4-(7-fluoro-5,6-dihydro-4H-pyrrolo[1,2-a][1,4]benzodiazepin-4-yl)phenyl]-ethanone,
1-[4-(7,10-dichloro-5,6-dihydro-4H-pyrrolo[1,2-a][1,4]benzodiazepin-4-yl)phenyl]-ethanone .HCl,
1-[4-(7,10-dichloro-5,6-dihydro-4H-pyrrolo[1,2-α][1,4]benzodiazepin-4-yl)phenyl]-ethanone,
1-[4-(10-chloro-5,6-dihydro-4H-pyrrolo[1,2-α][1,4]benzodiazepin-4-yl)phenyl]-ethanone,
1-[4-(7,9-difluoro-5,6-dihydro-4H-pyrrolo[1,2-α][1,4]benzodiazepin-4-yl)phenyl]-ethanone, and
1-[4-(7,9-difluoro-5,6-dihydro-4H-pyrrolo[1,2-α][1,4]benzodiazepin-4-yl)phenyl]-ethanone .HCl,
including any stereochemically isomeric form thereof,
and the pharmaceutically acceptable addition salts and the solvates thereof.

All possible combinations of the above-indicated interesting embodiments are considered to be embraced within the scope of this invention.

The present invention also encompasses processes for the preparation of compounds of Formula (I) and subgroups thereof.

The compounds of Formula (I) and the subgroups thereof can be prepared by a succession of steps as described hereunder. They are generally prepared from starting materials which are either commercially available or prepared by standard means obvious to those skilled in the art. The compounds of the present invention can be also prepared using standard synthetic processes commonly used by those skilled in the art of organic chemistry.

The compounds of the present invention wherein $R^{5a}$ is $C_{1-4}$alkylcarbonyl and wherein the other substituents are defined as before, can be prepared according to Scheme 1:

Scheme 1

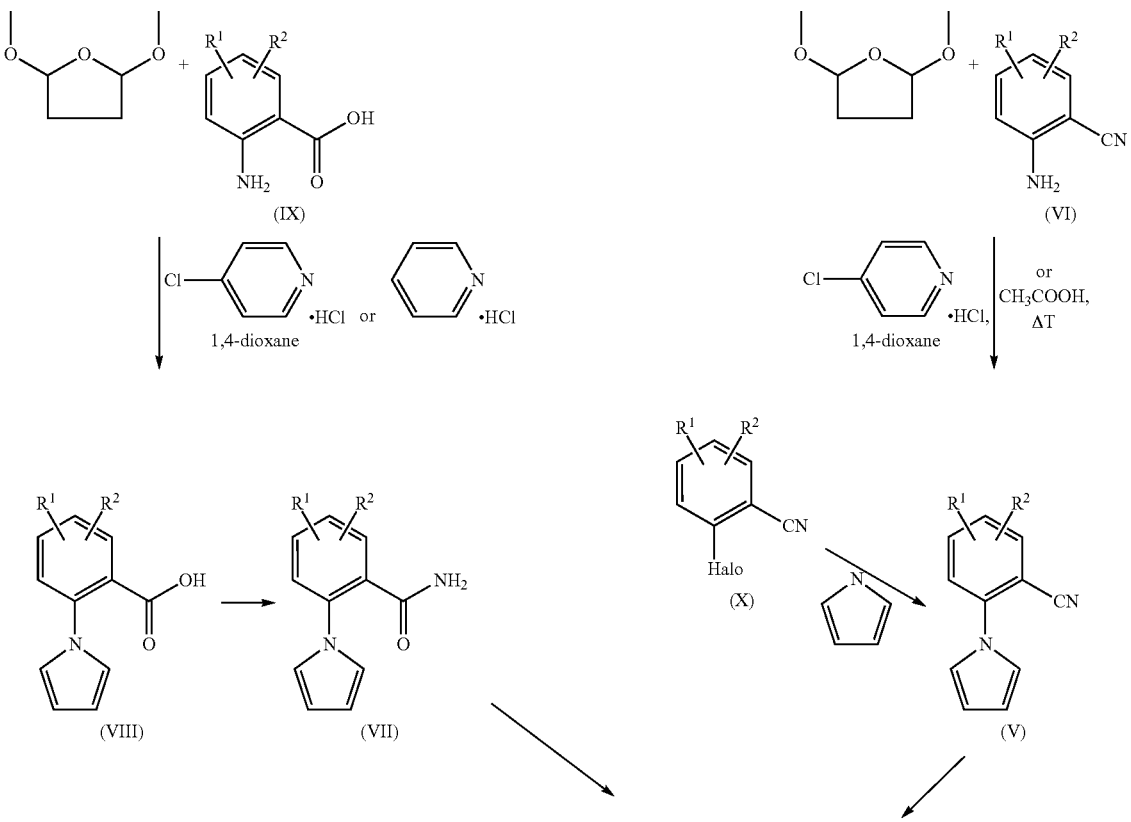

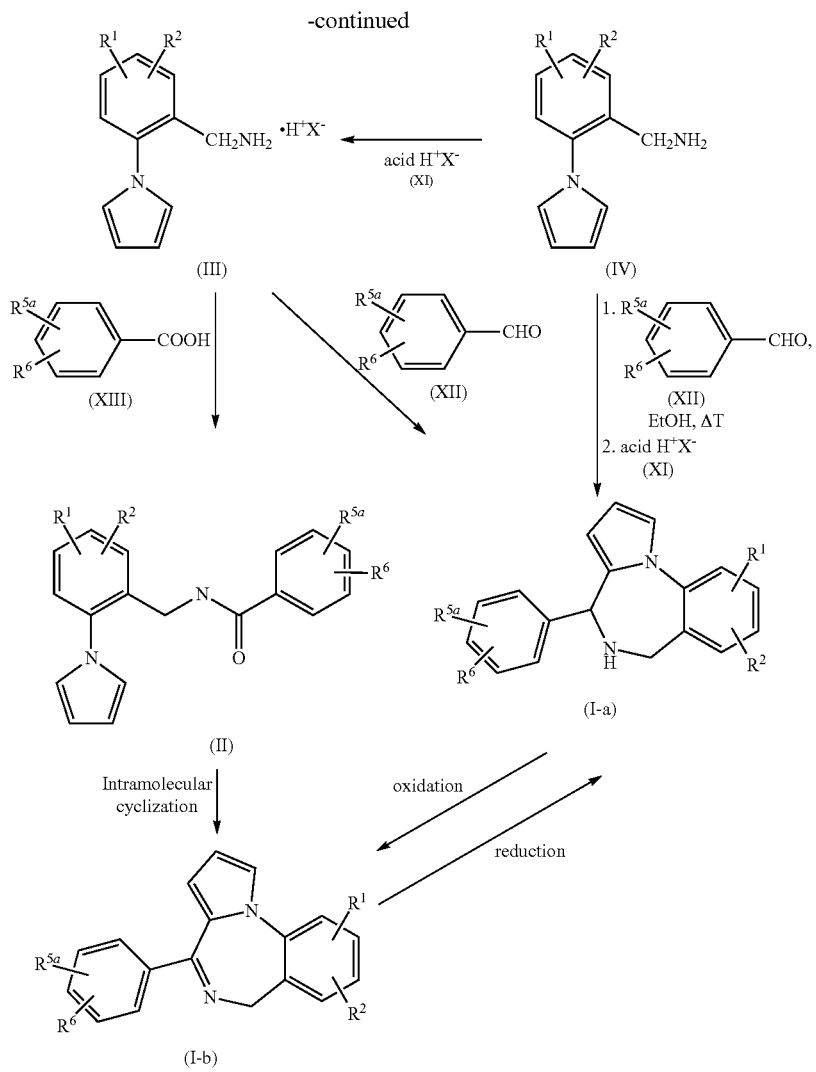

The compounds of Formula (I) wherein $R^3$ and $R^4$ together form an extra bond, said compounds being represented by formula (I-b), can be prepared from the compounds represented by the formula (I-a), following art-known amine to imine oxidation reactions. These oxidation reactions may be conducted by reacting a compound of formula (I-a) with an oxidant such as, for example, lead tetra-acetate or manganese dioxide, in a reaction inert solvent such as a halogenated hydrocarbon e.g. dichloromethane (DCM) or trichloromethane. The reaction rate can be enhanced by stirring and optionally heating the reaction mixture.

Alternatively, a compound of formula (I-b) can be prepared by an intramolecular cyclization of an intermediate of formula (II). In the presence of an acid such as, for example, $POCl_3$, the amide in the intermediate of formula (II) can function as a C-electrophile, resulting in a ring closure. The reaction may be performed in a suitable solvents such as, for example, DCM ($CH_2Cl_2$). Stirring and heating may enhance the rate of the reaction.

A compound of formula (I-a) can be prepared from an intermediate of formula (IV) by converting it in a salt (III) by reaction with an acid $H^+X^-$ of formula (XI), and reacting said salt of formula (III) with an aldehyde of formula (XII) in an appropriate solvent such as an alcohol, e.g. methanol (MeOH), ethanol (EtOH), isopropanol, at an elevated temperature, preferably at reflux temperature.

Alternatively, the intermediate of formula (IV) may be reacted first with the aldehyde of formula (XII) and the thus formed imine may be cyclized in the presence of an acid $H^+X^-$ of formula (XI) to a compound of formula (I-a).

Alternatively, a compound of formula (I-a) may be obtained by the reduction of a compound of formula (I-b) by using methods well-known to those skilled in the art.

An intermediate of formula (II) may be prepared by a coupling reaction between an intermediate of formula (III) and (XIII). Said reaction may be performed in the presence of coupling agents such as typically 1-hydroxy-1H-benzotriazole (HOBT) and N'-(ethylcarbonimidoyl)-N,N-dimethyl-1,3-propanediamine monohydrochloride (EDCI). The reaction may be performed in the presence of a base such as trietylamine ($Et_3N$) and a suitable solvent such as, for example, DCM. Alternatively, an acid chloride derivative of (XIII) or a reactive ester derivative of (XIII) can also be used in this type of reaction to prepare an intermediate of formula (II).

An intermediate of formula (XIII) or its acid chloride or ester derivative, can be easily prepared by those skilled in the art.

Intermediates of formula (III) and (IV) are prepared by reducing a 1-(2-cyano-phenyl)pyrrole derivative of formula (V). Several procedures well-known to those skilled in the art may be used to reduce the nitrile function such as, for example:

1. LiAlH$_4$/THF [S. Raines, S. Y. Chai and F. P. Palopoli; J. Heterocyclic Chem., 13, 711-716 (1976)]
2. i. sodium bis(2-methoxyethoxy)aluminate (Red-Al®) 70% w/w Toluene, RT:
   ii. NaOH 10%, RT [G. W. H. Cheeseman and S. G. Greenberg; J. Heterocyclic Chem., 16, 241-244 (1979)]
3a. i. KBH$_4$/CF$_3$COOH, THF; ii. H$_2$O; iii. HCl [P. Trinka, P. Siegel and J. Reiter; J. Prakt. Chem., 338, 675-678 (1996)]
3b. Borane-dimethyl sulfide (1:1), THF
4a. RaNi (Raney Nickel)/H$_2$
4b. RaNi/thiophene solution/(MeOH/NH$_3$)

Even other well-known methods for reducing the nitrile function may also be used.

An intermediate of formula (V) in turn is commercially available or alternatively can be easily prepared by, for example, treating a 2-aminobenzonitrile derivative of formula (VI) with tetrahydro-2,5-dimethoxyfuran in an inert solvent such as dioxane or tetrahydrofuran (THF) in the presence of an acid such as 4-chloropyridine hydrochloride, or in an acidic solvent such as glacial acetic acid, at an elevated temperature, preferably at reflux temperature. Alternatively, an intermediate of formula (V) can also be prepared from an intermediate of formula (X). Typically, an intermediate of formula (X) wherein Halo is defined as Br, I, Cl or F, is reacted with pyrrole in the presence of a base such as, for example, Cs$_2$CO$_3$ or NaH, in a suitable solvent such as typically DMF.

Alternatively, an intermediate of formula (IV) may be prepared by treating an intermediate of formula (VII) with borane-dimethyl sulfide (1:1) in a suitable solvent such as, for example, THF. The reaction typically can be performed in the presence of an acid such as HCl. After the reaction has proceeded, the reaction mixture can be basified with a suitable base such as NaOH. The reaction can be performed at an elevated temperature, preferably at reflux temperature.

An intermediate of formula (VII) can be prepared from an intermediate of formula (VIII). An intermediate of formula (VIII) can be reacted with a nitrogen source such as, NH$_3$.H$_2$O in the presence of HOBT and EDCI. This type of reaction typically can be performed in a suitable solvent like DMF. Stirring of the reaction mixture may enhance the rate of reaction.

An intermediate of formula (VIII) can be easily prepared by treating an intermediate of formula (IX) with tetrahydro-2,5-dimethoxyfuran in an inert solvent such as dioxane in the presence of an acid such as pyridine hydrochloride (1:1) at an elevated temperature, preferably at reflux temperature. Alternatively, a reactive ester derivative of (IX) can also be used in this type of reaction to prepare an intermediate of formula (VIII).

The compounds of the present invention according to formula (I-c), wherein R$^{5b}$ is defined as H—(CH$_2$)$_{1-3}$—CH(OH)— and wherein the other substituents are defined as before, can be prepared according to Scheme 2:

Scheme 2

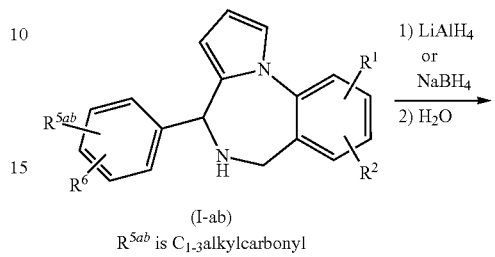

(I-ab)
R$^{5ab}$ is C$_{1-3}$alkylcarbonyl

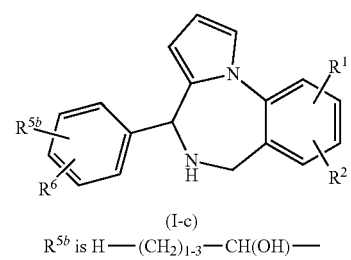

(I-c)
R$^{5b}$ is H—(CH$_2$)$_{1-3}$—CH(OH)—

A compound of formula (I-ab) may be prepared according to the reaction protocols described in Scheme 1. In formula (I-ab), R$^{5ab}$ is defined as C$_{1-3}$alkylcarbonyl and all other substituents are as defined before.

The carbonyl group of R$^{5ab}$ in compounds of formula (I-ab) can be reduced to obtain compounds according to formula (I-c). Typically this reaction can be performed in the presence of a reducing agent such as, for example, lithium aluminium hydride (LiAlH$_4$) or sodium borohydride (NaBH$_4$). This reaction may be carried out in the presence of a dried aprotic organic solvent, usually DCM, Et$_2$O or THF, followed by aqueous work-up.

Compounds of formula (I-f)

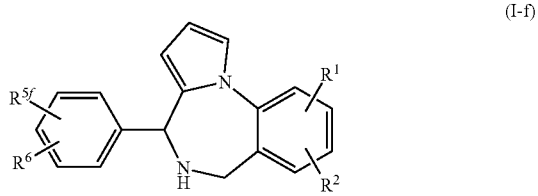

R$^{5f}$ is C$_{1-4}$alkyl substituted with one hydroxyl group wherein R$^{5f}$ represents C$_{1-4}$alkyl substituted with one hydroxyl moiety, may be prepared by using analogous reaction protocols as described in Scheme 1. In that case, an intermediate of formula (XII-a) may be used instead of an intermediate of formula (XII).

An intermediate of formula (XII-a) may be prepared according to well known protocols as shown in Scheme 2b. In a first step, the hydroxyl group of an intermediate of formula (XVIII) may be blocked by protecting groups (PG). They can be deprotected after a reaction step. Conventional protecting groups can be used in accordance with standard practice. Typically, the 2-tetrahydropyranyl group may be used as a protecting group for alcohols. In that case, an intermediate of formula (XVIII) may be reacted with dihydropyran in the presence of an acid such as, for example, PPTS (4-methyl-benzenesulfonic acid). In a second step, an intermediate of formula (XIX) is converted into an intermediate of formula (XII-a). This is typically done with n-butyllithium in aprotic anhydrous solvents e.g. THF in a first step, followed by addition of DMF in a second step. The reaction may be performed under an inert atmosphere such as, for example, $N_2$.

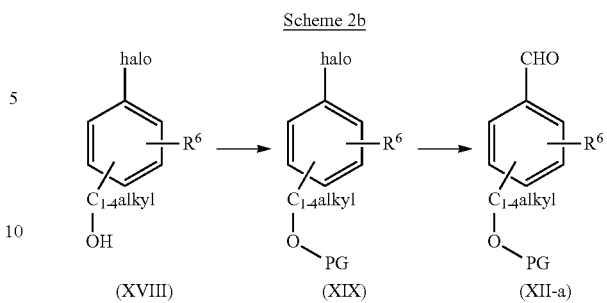

Scheme 2b

The compounds of the present invention wherein $R^{5c}$ is defined as $C_{1-4}$alkylsulphonyl and wherein the other substituents are defined as before, can be prepared according to Scheme 3:

Scheme 3

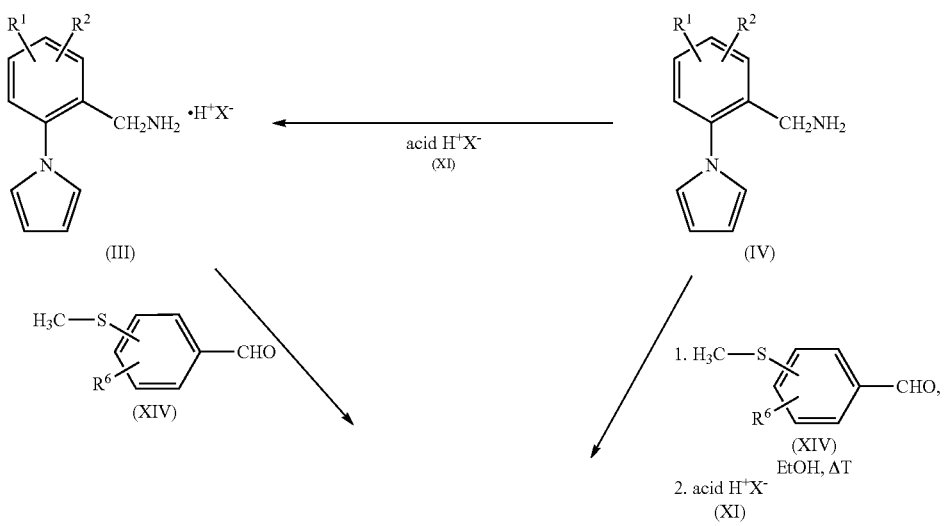

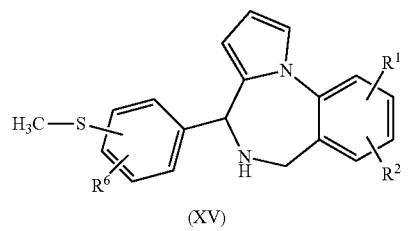

(XV)

↓ oxidation 1

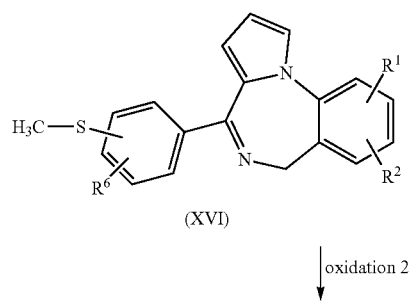

(XVI)

↓ oxidation 2

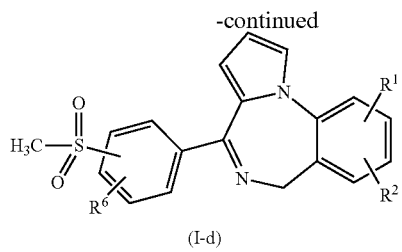

(I-d)

A compound of formula (I-d) can be prepared by oxidation of the sulphur group in an intermediate of formula (XVI). Typically, the reaction can be carried out in the presence of an oxidizing agent such as oxone and a suitable solvent such as, for example, THF.

An intermediate of formula (XVI) can be prepared from the intermediates represented by the formula (XV), following art-known amine to imine oxidation reactions. These oxidation reactions may be conducted by reacting an intermediate of formula (XV) with a mild oxidant such as, for example, lead tetra-acetate or manganese dioxide, in a reaction inert solvent such as a halogenated hydrocarbon e.g. dichloromethane (DCM) or trichloromethane. The reaction rate can be enhanced by stirring and optionally heating the reaction mixture.

An intermediate of formula (XV) can be prepared from an intermediate of formula (IV) by converting it in a salt (III) by reaction with an acid $H^+X^-$ of formula (XI), and reacting said salt of formula (III) with an aldehyde of formula (XIV) in an appropriate solvent such as an alcohol, e.g. methanol (MeOH), ethanol (EtOH), isopropanol, at an elevated temperature, preferably at reflux temperature.

Alternatively, the intermediate of formula (IV) may be reacted first with the aldehyde of formula (XIV) and the thus formed imine may be cyclized in the presence of an acid $H^+X^-$ of formula (XI) to an intermediate of formula (XV).

Compounds of formula (I-e)

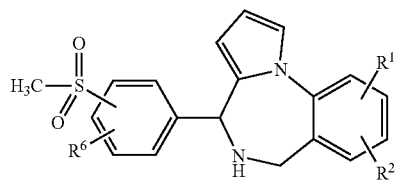

(I-e)

may be prepared by using analoguous reactions as described in Scheme 3 for intermediate (XV), but starting from an intermediate of formula (XVII)

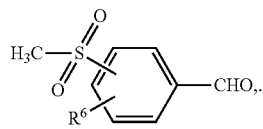

(XVII)

Alternatively compounds of formula (I-e) may be prepared from intermediates of formula (XV). In this type of reaction, the NH group of the intermediate of formula (XV) is first protected with a amine protecting group such as typically tert-butyloxycarbonyl, benzyl or tosyl, and subsequently the sulphur is oxidized by using reaction conditions such as described for 'oxidation 2' in Scheme 3. Finally the protected NH group is deprotected.

All starting materials are commercially available or can be easily prepared by those skilled in the art.

In all these preparations, the reaction products may be isolated from the reaction medium and, if necessary, further purified according to methodologies generally known in the art such as, for example, extraction, crystallization, trituration and chromatography. In particular, stereoisomers can be isolated chromatographically using a chiral stationary phase such as, for example, Chiralpak® AD (amylose 3,5 dimethylphenyl carbamate) or Chiralpak® AS, both purchased from Daicel Chemical Industries, Ltd, in Japan.

Pure stereoisomeric forms of the compounds and the intermediates of this invention may be obtained by the application of art-known procedures. Enantiomers may be separated from each other by the selective crystallization of their diastereomeric salts with optically active acids. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably if a specific stereoisomer is desired, said compound will be synthesized by stereoselective or stereospecific methods of preparation. These methods will advantageously employ chirally pure starting materials. Stereoisomeric forms of the compounds of Formula (I) are obviously intended to be included within the scope of the invention.

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

The compounds of Formula (I) and stereoisomeric forms thereof, and the pharmaceutically acceptable addition salts, and the solvates thereof, may be active against dematiaceous hyphomycetes, dimorphic pathogens, dermatophytes, zygomycetes, hyaline hyphomycetes, yeasts and yeastlike organisms.

The compounds of Formula (I) and stereoisomeric forms thereof, and the pharmaceutically acceptable addition salts, and the solvates thereof, may be active against dimorphic pathogens, yeasts and yeastlike organisms.

The compounds of Formula (I) and stereoisomeric forms thereof, and the pharmaceutically acceptable addition salts, and the solvates thereof, may be active against moulds.

The compounds of Formula (I) and stereoisomeric forms thereof, and the pharmaceutically acceptable addition salts, and the solvates thereof, may be active against a wide variety of fungi, such as *Candida* spp., e.g. *Candida albicans, Can-* dida glabrata, Candida krucei; Candida parapsilosis, Candida kefyr, Candida tropicalis; Aspergillus spp., e.g. Aspergillus fumigatus, Aspergillus niger, Aspergillus flavus; Cryptococcus neoformans; Sporothrix schenckii; Epidermophyton floccosum; Microsporum spp., e.g. Microsporum canis, Microsporum gypseum; Trichophyton spp., e.g. Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium spp., e.g. Fusarium solani, Fusarium oxysporum, Fusarium proliferatum, Fusarium verticillioides; Rhizomucor spp., e.g. Rhizomucor miehei, Rhizomucor pusillus; Mucor circinelloides; Rhizopus spp., e.g. Rhizopus oryzae, Rhizopus microspores; Malassezia furfur; Acremonium spp.; Paecilomyces; Scopulariopsis; Arthrographis spp.; Scytalidium; Scedosporium spp., e.g. Scedosporium apiospermum, Scedosporium prolificans; Trichoderma spp.; Penicillium spp.; Penicillium marneffei; Blastoschizomyces.

The compounds of Formula (I) and stereoisomeric forms thereof, and the pharmaceutically acceptable addition salts, and the solvates thereof, may be active against a wide variety of fungi, such as Candida parapsilosis; Aspergillus spp., e.g. Aspergillus fumigatus, Aspergillus niger, Aspergillus flavus; Cryptococcus neoformans; Sporothrix schenckii; Epidermophyton floccosum; Microsporum spp., e.g. Microsporum canis, Microsporum gypseum; Trichophyton spp., e.g. Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium spp., e.g. Fusarium solani, Fusarium oxysporum, Fusarium proliferatum, Fusarium verticillioides; Rhizomucor spp., e.g. Rhizomucor miehei, Rhizomucor pusillus; Mucor circinelloides; Rhizopus spp., e.g. Rhizopus oryzae, Rhizopus microspores; Acremonium spp.; Paecilomyces; Scopulariopsis; Arthrographis spp.; Scytalidium; Scedosporium spp., e.g. Scedosporium apiospermum, Scedosporium prolificans; Trichoderma spp.; Penicillium spp.; Penicillium marneffei; Blastoschizomyces.

The compounds of Formula (I) and stereoisomeric forms thereof, and the pharmaceutically acceptable addition salts, and the solvates thereof, may be active against a wide variety of fungi, such as Candida parapsdosis; Aspergillus spp., e.g. Aspergillus fumigatus, Aspergillus niger, Aspergillus flavus; Cryptococcus neoformans; Epidermophyton floccosum; Microsporum spp., e.g. Microsporum canis, Microsporum gypseum; Trichophyton spp., e.g. Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium spp., e.g. Fusarium solani, Fusarium oxysporum, Fusarium proliferatum, Fusarium verticillioides; Rhizomucor spp., e.g. Rhizomucor miehei, Rhizomucor pusillus; Mucor circinelloides; Rhizopus spp., e.g. Rhizopus oryzae, Rhizopus microspores; Acremonium spp.; Paecilomyces; Scopulariopsis; Arthrographis spp.; Scytalidium; Scedosporium spp., e.g. Scedosporium apiospermum, Scedosporium prolificans; Trichoderma spp.; Penicillium spp.; Penicillium marneffei; Blastoschizomyces; in particular Aspergillus spp., e.g. Aspergillus fumigatus, Aspergillus niger, Aspergillus flavus; Cryptococcus neoformans; Epidermophyton floccosum; Microsporum spp., e.g. Microsporum canis, Microsporum gypseum; Trichophyton spp., e.g. Trichophyton mentagrophytes, Trichophyton rubrum, Trichophyton quinckeanum, Trichophyton tonsurans, Trichophyton verrucosum, Trichophyton violaceum, Trichophyton interdigitale, Trichophyton soudanense; Fusarium spp., e.g. Fusarium solani, Fusarium oxysporum, Fusarium proliferatum, Fusarium verticillioides; Rhizomucor spp., e.g. Rhizomucor miehei, Rhizomucor pusillus; Mucor circinelloides; Rhizopus spp., e.g. Rhizopus oryzae, Rhizopus microspores; Acremonium spp.; Paecilomyces; Scopulariopsis; Arthrographis spp.; Scytalidium; Scedosporium spp., e.g. Scedosporium apiospermum, Scedosporium prolificans; Trichoderma spp.; Penicillium spp.; Penicillium marneffei; Blastoschizomyces.

The compounds of Formula (I) and stereoisomeric forms thereof, and the pharmaceutically acceptable addition salts, and the solvates thereof, may be active against a wide variety of fungi, such as Candida parapsilosis; Aspergillus spp.; Cryptococcus neoformans; Sporothrix schenckii; Microsporum spp.; Fusarium spp.; Scedosporium spp.;
in particular Candida parapsilosis; Aspergillus spp.; Cryptococcus neoformans; Microsporum spp.; Fusarium spp.; Scedosporium spp.;
more in particular Aspergillus spp.; Cryptococcus neoformans; Microsporum spp.; Fusarium spp.; Scedosporium spp.

The compounds of Formula (I) and stereoisomeric forms thereof, and the pharmaceutically acceptable addition salts, and the solvates thereof, may be active against a wide variety of fungi, such as Candida parapsilosis; Aspergillus spp.; Cryptococcus neoformans; Trichophyton spp.; Sporothrix schenckii; Microsporum spp.; Fusarium spp.; Scedosporium spp.;
in particular Aspergillus spp.; Microsporum spp.; Trichophyton spp.

The compounds of Formula (I) and stereoisomeric forms thereof, and the pharmaceutically acceptable addition salts, and the solvates thereof, may be active against fungi such as Candida parapsilosis; Aspergillus spp., e.g. Aspergillus fumigatus, Aspergillus niger, Aspergillus flavus; Cryptococcus neoformans; Sporothrix schenckii; Epidermophyton floccosum; Microsporum canis; Trichophyton spp., e.g. Trichophyton mentagrophytes, Trichophyton rubrum, Trichophyton quinckeanum; in particular Candida parapsilosis; Aspergillus spp., e.g. Aspergillus fumigatus, Aspergillus niger, Aspergillus flavus; Cryptococcus neoformans; Epidermophyton floccosum; Microsporum canis; Trichophyton spp., e.g. Trichophyton mentagrophytes, Trichophyton rubrum, Trichophyton quinckeanum;
more in particular Aspergillus spp., e.g. Aspergillus fumigatus, Aspergillus niger, Aspergillus flavus; Cryptococcus neoformans; Epidermophyton floccosum; Microsporum canis; Trichophyton spp., e.g. Trichophyton mentagrophytes, Trichophyton rubrum, Trichophyton quinckeanum.

The compounds of Formula (I) and stereoisomeric forms thereof, and the pharmaceutically acceptable addition salts, and the solvates thereof, may be active against Candida parapsilosis, Aspergillus fumigatus, Cryptococcus neoformans, Sporothrix schenckii, Microsporum canis, Trichophyton mentagrophytes, Trichophyton rubrum, Scedosporium apiospermum and Scedosporium prolificans; in particular Aspergillus fumigatus, Microsporum canis, Trichophyton mentagrophytes, Trichophyton rubrum, Scedosporium apiospermum and Scedosporium prolificans.

The compounds of Formula (I) and stereoisomeric forms thereof, and the pharmaceutically acceptable addition salts, and the solvates thereof, may be active against fungi such as Candida parapsilosis; Aspergillus spp.; Cryptococcus neoformans; Microsporum spp.; Trichophyton spp.; Scedosporium spp.

The compounds of Formula (I) and stereoisomeric forms thereof, and the pharmaceutically acceptable addition salts, and the solvates thereof, may be active against *Candida parapsilosis, Aspergillus fumigatus, Cryptococcus neoformans, Sporothrix schenckii, Microsporum canis, Trichophyton mentagrophytes, Trichophyton rubrum, Scedosporium apiospermum, Scedosporium prolificans;* in particular *Candida parapsilosis, Aspergillus fumigatus, Cryptococcus neoformans, Microsporum canis, Trichophyton mentagrophytes, Trichophyton rubrum, Scedosporium apiospermum* and *Scedosporium prolificans;* more in particular *Aspergillus fumigatus, Cryptococcus neoformans, Microsporum canis, Trichophyton mentagrophytes, Trichophyton rubrum, Scedosporium apiospermum* and *Scedosporium prolificans.*

The compounds of Formula (I) and stereoisomeric forms thereof, and the pharmaceutically acceptable addition salts, and the solvates thereof, may be active against *Candida parapsilosis, Aspergillus fumigatus, Cryptococcus neoformans, Sporothrix schenckii, Microsporum canis, Trichophyton mentagrophytes, Trichophyton rubrum, Scedosporium apiospermum, Scedosporium prolificans, Rhizopus oryzae, Rhizomucor miehei, Mucor circinelloides.*

The compounds of Formula (I) and stereoisomeric forms thereof, and the pharmaceutically acceptable addition salts, and the solvates thereof, may be active against *Candida parapsilosis* B66126, *Aspergillus fumigatus* B42928, *Cryptococcus neoformans* B66663, *Sporothrix schenckii* B62482, *Microsporum canis* B68128, *Trichophyton mentagrophytes* B70554, *Trichophyton rubrum* B68183, *Scedosporium apiospermum* IHEM3817, *Scedosporium prolificans* IHEM21157.

The compounds of Formula (I) and stereoisomeric forms thereof, and the pharmaceutically acceptable addition salts, and the solvates thereof, may be active against *Candida parapsilosis* B66126, *Aspergillus fumigatus* B42928, *Cryptococcus neoformans* B66663, *Sporothrix schenckii* B62482, *Microsporum canis* B68128, *Trichophyton mentagrophytes* B70554, *Trichophyton rubrum* B68183, *Scedosporium apiospermum* IHEM3817, *Scedosporium prolificans* IHEM21157, *Rhizopus oryzae* IHEM5223, *Rhizomucor miehei* IHEM13391 and *Mucor circinelloides* IHEM21105.

The compounds of Formula (I) and stereoisomeric forms thereof, and the pharmaceutically acceptable addition salts, and the solvates thereof, may be active against a variety of fungi that infect the skin, hair and nails, as well as subcutaneous and systemic fungal pathogens.

The compounds of Formula (I) and stereoisomeric forms thereof, and the pharmaceutically acceptable addition salts, and the solvates thereof, may be active against the 3 dermatophyte genera: *Trichophyton, Microsporum* and *Epidermophyton*; in particular against *Trichophyton* and *Microsporum*.

The compounds of Formula (I) and stereoisomeric forms thereof, and the pharmaceutically acceptable addition salts, and the solvates thereof, may be active against dermatophytes and *Aspergillus* spp.; in particular dermatophytes and *Aspergillus fumigatus*; more in particular *Microsporum canis, Trichophyton mentagrophytes, Trichophyton rubrum* and *Aspergillus fumigatus*; even more in particular *Microsporum canis, Trichophyton mentagrophytes* and *Trichophyton rubrum*.

The compounds of Formula (I) and stereoisomeric forms thereof, and the pharmaceutically acceptable addition salts, and the solvates thereof, may be active against *Trichophyton mentagrophytes, Trichophyton rubrum* and *Aspergillus* spp.; in particular *Trichophyton mentagrophytes, Trichophyton rubrum* and *Aspergillus fumigatus*.

The compounds of Formula (I) and stereoisomeric forms thereof, and the pharmaceutically acceptable addition salts, and the solvates thereof, may be active against *Trichophyton mentagrophytes; Trichophyton rubrum; Aspergillus* spp., e.g. *Aspergillus fumigatus; Fusarium* spp.; *Mucor* Spp.; *Zygomycetes* spp.; *Scedosporium* spp.; *Microsporum canis; Sporothrix schenckii; Cryptococcus neoformans* and *Candida parapsilosis.*

The compounds of Formula (I) and stereoisomeric forms thereof, and the pharmaceutically acceptable addition salts, and the solvates thereof, may be active against dermatophytes.

The compounds of Formula (I) and stereoisomeric forms thereof, and the pharmaceutically acceptable addition salts, and the solvates thereof, may be active against *Aspergillus fumigatus.*

The compounds of Formula (I) and stereoisomeric forms thereof, and the pharmaceutically acceptable addition salts, and the solvates thereof, may be active against *Microsporum canis*, in particular *Microsporum canis* B68128.

The compounds of Formula (I) and stereoisomeric forms thereof, and the pharmaceutically acceptable addition salts, and the solvates thereof, may be active against *Trichophyton rubrum*, in particular *Trichophyton rubrum* B68183.

The compounds of Formula (I) and stereoisomeric forms thereof, and the pharmaceutically acceptable addition salts, and the solvates thereof, may be active against a wide variety of fungi, such as one or more of the fungi mentioned hereinbefore.

The compounds of Formula (I) and stereoisomeric forms thereof, and the pharmaceutically acceptable addition salts, and the solvates thereof, are potent antifungals when administered orally or topically.

The compounds of the present invention may be useful as ergosterol synthesis inhibitors.

In view of the utility of the compound of Formula (I), there is provided a method of treating warm-blooded animals, including humans, suffering from, or a method of preventing warm-blooded animals, including humans, to suffer from any one of the diseases mentioned hereinbefore. Hence, compounds of Formula (I) are provided for use as a medicine. Also the use of a compound of Formula (I) in the manufacture of a medicament useful in treating fungal infections is provided. Further compounds of Formula (I) are provided for use in the treatment of fungal infections As used herein, the term "treatment" is intended to refer to all processes, wherein there may be a slowing, interrupting, arresting, or stopping of the progression of an infection, but does not necessarily indicate a total elimination of all symptoms.

The invention relates to a compound according to the general Formula (I), the stereoisomeric forms thereof and the pharmaceutically acceptable acid or base addition salts and the solvates thereof, for use as a medicament.

The invention also relates to a compound according to the general Formula (I), the stereoisomeric forms thereof and the pharmaceutically acceptable acid or base addition salts and the solvates thereof, for the treatment or prevention of fungal infections; in particular fungal infections caused by one or more of the fungi mentioned hereinbefore.

The invention also relates to a compound according to the general Formula (I), the stereoisomeric forms thereof and the pharmaceutically acceptable acid or base addition salts and the solvates thereof, for the treatment of fungal infections; in particular fungal infections caused by one or more of the fungi mentioned hereinbefore.

The invention also relates to a compound according to the general Formula (I), the stereoisomeric forms thereof and the pharmaceutically acceptable acid or base addition salts and the solvates thereof, for use in the treatment or prevention of fungal infections; in particular fungal infections caused by one or more of the fungi mentioned hereinbefore.

The invention also relates to a compound according to the general Formula (I), the stereoisomeric forms thereof and the pharmaceutically acceptable acid or base addition salts and the solvates thereof, for use in the treatment of fungal infections; in particular fungal infections caused by one or more of the fungi mentioned hereinbefore.

The invention also relates to a compound according to the general Formula (I), the stereoisomeric forms thereof and the pharmaceutically acceptable acid or base addition salts and the solvates thereof, for use in the treatment or prevention, in particular treatment, of fungal infections; in particular fungal infections caused by one or more of the fungi selected from a group consisting of fungi mentioned hereinbefore.

The invention also relates to a compound according to the general Formula (I), the stereoisomeric forms thereof and the pharmaceutically acceptable acid or base addition salts and the solvates thereof, for use in the treatment or prevention of a fungal infection, in particular a fungal infection caused by one or more of the fungi mentioned hereinbefore.

The invention also relates to a compound according to the general Formula (I), the stereoisomeric forms thereof and the pharmaceutically acceptable acid or base addition salts and the solvates thereof, for use in the treatment or prevention of a fungal infection, wherein the fungal infection is caused by one or more of the fungi selected from the group consisting of *Candida* spp.; *Aspergillus* spp.; *Cryptococcus neoformans; Sporothrix schenckii; Epidermophyton floccosum; Microsporum* spp.; *Trichophyton* spp; *Fusarium* spp.; *Rhizomucor* spp.; *Mucor circinelloides; Rhizopus* spp.; *Malassezia furfur; Acremonium* spp.; *Paecilomyces; Scopulariopsis; Arthrographis* spp.; *Scytalidium; Scedosporium* spp.; *Trichoderma* spp.; *Penicillium* spp.; *Penicillium marneffei*; and *Blastoschizomyces;*
in particular wherein the fungal infection is caused by one or more of the fungi selected from the group consisting of *Candida parapsdosis; Aspergillus* spp.; *Cryptococcus neoformans; Sporothrix schenckii; Epidermophyton floccosum; Microsporum* spp.; *Trichophyton* spp.; *Fusarium* spp.; *Rhizomucor* spp.; *Mucor circinelloides; Rhizopus* spp.; *Acremonium* spp.; *Paecilomyces; Scopulariopsis; Arthrographis* spp.; *Scytalidium; Scedosporium* spp.; *Trichoderma* spp.; *Penicillium* spp.; *Penicillium marneffei*; and *Blastoschizomyces;*
even more in particular wherein the fungal infection is caused by one or more of the fungi selected from the group consisting of *Microsporum canis, Trichophyton mentagrophytes, Trichophyton rubrum* and *Aspergillus fumigatus.*

The novel compounds described in the present invention may be useful in the treatment or prevention of diseases or conditions selected from the group consisting of infections caused by dermatophytes, systemic fungal infections and onychomycosis.

The novel compounds described in the present invention may be useful in the treatment or prevention of diseases or conditions such as for example infections caused by dermatophytes, systemic fungal infections or onychomycosis.

The invention also relates to the use of a compound according to the general Formula (I), the stereoisomeric forms thereof and the pharmaceutically acceptable acid or base addition salts and the solvates thereof, for the manufacture of a medicament.

The invention also relates to the use of a compound according to the general Formula (I), the stereoisomeric forms thereof and the pharmaceutically acceptable acid or base addition salts and the solvates thereof, for the manufacture of a medicament for the treatment or prevention, in particular treatment, of fungal infections, in particular fungal infections caused by one or more of the fungi mentioned hereinbefore.

The compounds of the present invention can be administered to mammals, preferably humans, for the treatment or prevention, in particular treatment, of fungal infections, in particular fungal infections caused by one or more of the fungi mentioned hereinbefore.

In view of the utility of the compound of Formula (I), there is provided a method of treating warm-blooded animals, including humans, suffering from or a method of preventing warm-blooded animals, including humans, to suffer from fungal infections, in particular fungal infections caused by one or more of the fungi mentioned hereinbefore.

Said methods comprise the administration, i.e. the systemic or topical administration, preferably oral administration, of an effective amount of a compound of Formula (I), a stereoisomeric form thereof or a pharmaceutically acceptable addition salt or solvate thereof, to warm-blooded animals, including humans.

Said methods comprise the administration, i.e. the systemic or topical administration, preferably oral administration, of an effective amount of a compound of Formula (I), to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

While it is possible for the active ingredient to be administered alone, it is preferable to present it as a pharmaceutical composition.

The present invention also provides compositions for treating or preventing fungal infections comprising a therapeutically effective amount of a compound of Formula (I) and a pharmaceutically acceptable carrier or diluent.

The carrier or diluent must be "acceptable" in the sense of being compatible with the other ingredients of the composition and not deleterious to the recipients thereof.

The compounds of the present invention, that are suitable to treat or prevent fungal infections, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

In view of their useful pharmacological properties, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

Transungual compositions are in the form of a solution and the carrier optionally comprises a penetration enhancing agent which favours the penetration of the antifungal into and through the keratinized ungual layer of the nail. The solvent medium comprises water mixed with a co-solvent such as an alcohol having from 2 to 6 carbon atoms, e.g. ethanol.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The ratio of active ingredient over cyclodextrin may vary widely. For example ratios of 1/100 to 100/1 may be applied. Interesting ratios of active ingredient over cyclodextrin range from about 1/10 to 10/1. More interesting ratios of active ingredient over cyclodextrin range from about 1/5 to 5/1.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

For parenteral compositions, also other ingredients, to aid solubility for example, e.g. cyclodextrins, may be included. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of Formula (I) and one or more appropriate pharmaceutically acceptable water-soluble polymers.

The term "a solid dispersion" defines a system in a solid state (as opposed to a liquid or gaseous state) comprising at least two components, in casu the compound of Formula (I)

and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastro-intestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of Formula (I), or amorphous, microcrystalline or crystalline water-soluble polymer, or both, are dispersed more or less evenly in another phase comprising water-soluble polymer, or compound of Formula (I), or a solid solution comprising compound of Formula (I) and water-soluble polymer. Said domains are regions within the solid dispersion distinctively marked by some physical feature, small in size, and evenly and randomly distributed throughout the solid dispersion.

It may further be convenient to formulate the present antifungal compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antifungal agent but do not chemically bond to the antifungal agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the present antifungals are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and an antifungal agent and a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage.

Unit dosage form as used in the specification and claims herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions, teaspoonfuls, tablespoonfuls and the like, and segregated multiples thereof.

Since the compounds according to the invention are potent orally administrable compounds, pharmaceutical compositions comprising said compounds for administration orally are especially advantageous.

The following examples illustrate the present invention.

EXPERIMENTAL PART

Hereinafter, the term "DCM" means dichloromethane; "LCMS" means Liquid Chromatography/Mass spectrometry; "TLC" means thin layer chromatography; "DIPE" means diisopropyl ether; "PE" means petroleum ether; "TFA" means trifluoroacetic acid; "HPLC" means high-performance liquid chromatography; "r.t." means room temperature; "m.p." means melting point; "min" means minute(s); "h" means hour(s); "EtOAc" means ethyl acetate; "EtOH" means ethanol; "r.m." means reaction mixture(s); "q.s." quantum sufficit; "THF" means tetrahydrofuran; "HOAc" means acetic acid; "HOBT" means 1-hydroxy-1H-benzotriazole; "Me$_2$S" means dimethyl sulfide; "PPTS" means 4-methylbenzenesulfonic acid, compound with pyridine (1:1); "DHP" means dihydropyran; and "EDCI" means N'-(ethylcarbonimidoyl)-N,N-dimethyl-1,3-propanediamine monohydrochloride. The person skilled in the art will realize that for some reactions in the examples anhydrous conditions need to be applied and/or an inert protecting atmosphere such as, for example, N$_2$ or argon, must be used.

A. Preparation of the Intermediates

Example A1 a) Preparation of Intermediate 1

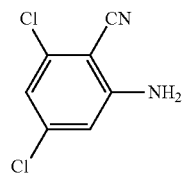 [SMILES: N#Cc1c(N)cc(Cl)cc1Cl]

2-Amino-4,6-dichlorobenzamide (30 g, 0.15 mol) was dissolved in POCl$_3$ (108 g, 0.7 mol). The solution was stirred at 100° C. for 2 h, and was then poured into ice. The obtained mixture was filtered and dried. The residue was purified by column chromatography over silica gel (eluent: PE/EtOAc 20/1). The desired fractions were collected and the solvent was evaporated, to yield 10.5 g of intermediate 1 (37.5% yield).

b) Preparation of Intermediate 2

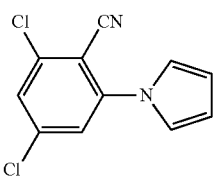 [SMILES: N#Cc1c(Cl)cc(Cl)cc1-n1cccc1]

A mixture of intermediate 1 (8.13 g, 0.043 mol) and tetrahydro-2,5-dimethoxyfuran (6.55 g, 0.049 mol) in HOAc (80 ml) was stirred and refluxed until the reaction was completed (followed by TLC). The mixture was cooled and evaporated. The residue was purified by column chromatography (eluent: DIPE/EtOAc 20/1). The desired fractions were collected and the solvent was evaporated, yielding 8.2 g of intermediate 2 (80.5% yield).

c) Preparation of Intermediate 3

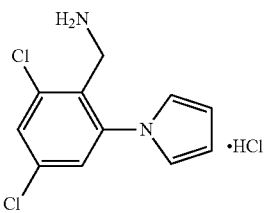 [SMILES: NCc1c(Cl)cc(Cl)cc1-n1cccc1 ; Cl]

Borane-dimethyl sulphide (1:1) (3.1 ml of a 10 M solution of $BH_3$ in $Me_2S$, 0.03 mol) was added dropwise to a mixture of intermediate 2 (6.52 g, 0.0275 mol) and THF (50 ml) under $N_2$ atmosphere. The r.m. was heated at reflux temperature for 10 h. Subsequently, the mixture was cooled to r.t., and HCl (6 N) was added dropwise. The mixture was heated at reflux temperature again for 30 min, and was then cooled to 0° C. NaOH (6 N) was added and the liberated amine was extracted with EtOAc. The separated organic layer was dried ($Na_2SO_4$), filtered and the solvent was evaporated. HCl in dioxane (q.s.) was added and evaporated again. The product was washed with DCM. Yield: 6.5 g of intermediate 3 (85.5%; .HCl).

Example A2 a) Preparation of Intermediate 4

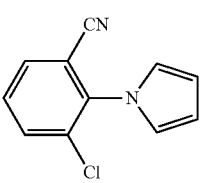 [SMILES: N#Cc1cccc(Cl)c1-n1cccc1]

A mixture of 3-chloro-2-fluoro-benzonitrile (25 g, 160.7 mmol), pyrrole (12.94 g, 192.8 mmol) and $Cs_2CO_3$ (62.81 g, 192.8 mmol) in DMF (150 ml) was stirred overnight at 100° C. The mixture was cooled and poured into ice-water. The solid was filtered off and dissolved in DCM. The solution was dried ($Na_2SO_4$), filtered and evaporated to yield 29 g of intermediate 4 (90.1% yield).

b) Preparation of Intermediate 5

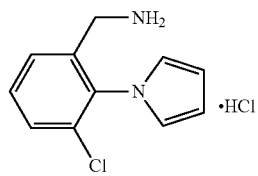 [SMILES: NCc1cccc(Cl)c1-n1cccc1 ; Cl]

Intermediate 4 (29 g, 143 mmol) was dissolved in THF (200 ml). A 10 M $BH_3.Me_2S$ solution (15.45 ml, 154.5 mmol) was added slowly to the solution under $N_2$ atmosphere. The r.m. was stirred and refluxed overnight. Then, the mixture was cooled and acidified with 6 N HCl until pH 1. Subsequently, the mixture was stirred and refluxed for 30 min. The mixture was cooled again and poured into ice-water. This mixture was adjusted to pH 8-9 with NaOH, and was then extracted with EtOAc. The separated organic layer was dried ($Na_2SO_4$), filtered and concentrated. The residue was dissolved in HCl/dioxane. The solvent was evaporated under reduced pressure. The residue was washed with DCM (50 ml). The solid was filtered off and dried in vacuo. Yield: 22 g of intermediate 5 (64.7% yield; .HCl).

Example A3 a) Preparation of Intermediate 6

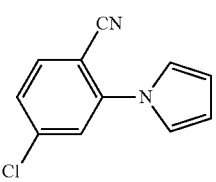 [SMILES: N#Cc1ccc(Cl)cc1-n1cccc1]

Tetrahydro-2,5-dimethoxyfuran (49.9 g, 0.378 mol) was added to a solution of 2-amino-4-chlorobenzonitrile (50.0 g, 0.328 mol) in HOAc (300 ml). The r.m. was stirred and refluxed for 2 h, and was then cooled. Subsequently the solvent was evaporated. The residue was purified by flash column chromatography over silica gel (eluent: DCM). The product fractions were collected and the solvent was evaporated. Yield: 13 g of intermediate 6 (98.4% yield).

b) Preparation of Intermediate 7

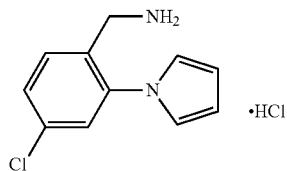 [SMILES: NCc1ccc(Cl)cc1-n1cccc1 ; Cl]

Intermediate 6 (33 g, 0.163 mol) was dissolved in THF (250 ml). A 10 M solution of $BH_3$ in $Me_2S$ (17.6 ml, 0.176 mol) was added slowly to the solution under N₂ atmosphere. The r.m. was stirred and refluxed overnight. Subsequently, the mixture was cooled and acidified with a 6 N HCl solution to pH 1. The mixture was stirred and refluxed again for 30 min. The mixture was cooled and poured into ice-water. This mixture was adjusted to pH 8-9 with NaOH, and was then extracted with EtOAc. The separated organic layer was dried (Na₂SO₄), filtered and the solvent was evaporated. The residue was dissolved in HCl/dioxane. The solvent of this solution was evaporated and the residue was washed with DCM (50 ml). The solid was filtered off and dried in vacuo. Yield: 23.5 g of intermediate 7 (59.4% yield; .HCl).

Example A4 a) Preparation of Intermediate 8

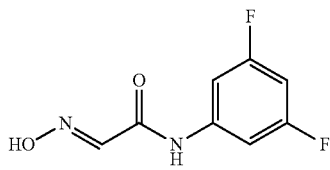 [SMILES: O=C(/C=N/O)Nc1cc(F)cc(F)c1]

A mixture of 3,5-difluorobenzenamine (129 g, 1.00 mol) and concentrated HCl (350 ml) in H₂O (1 l) was added to a mixture of 2,2,2-trichloro-acetaldehyde (179 g, 1.22 mol) and Na₂SO₄ (1500 g) in H₂O (2 l). Subsequently, NH₂OH.HCl (207 g, 3.00 mol) in H₂O (500 ml) was added and the r.m. was heated to reflux for 1 h. Then, the r.m. was cooled to 0° C. The solid was collected and dissolved in EtOAc. This solution was dried (Na₂SO₄), filtered and the solvent was evaporated to yield a grey solid. Yield: 160 g of intermediate 8 (80% yield).

b) Preparation of Intermediate 9

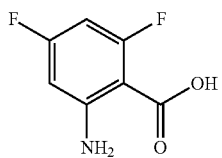

Intermediate 8 (160 g, 0.8 mol) was added portionwise to conc. H₂SO₄ (1 l) at 50° C. The solution was heated to 100° C. for 2 h, and was then poured into ice-water (3 l). The precipitate (approximately 0.8 mol) was collected and was dissolved in 1 N NaOH (2 l). H₂O₂ (300 ml) was added to this solution at 0° C., and after allowing the r.m. to reach r.t. it was stirred overnight. Subsequently, the mixture was filtered and 2N HCl was added to the filtrate until pH 1. The precipitate was filtered off and dissolved in EtOAc (2 l). The solution was dried (Na₂SO₄), filtered and the solvent was evaporated to yield 120 g of intermediate 9 (83% yield) as a yellow solid.

c) Preparation of Intermediate 10

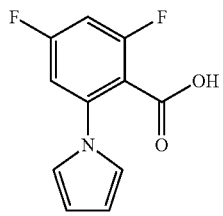

A mixture of intermediate 9 (60.0 g, 0.346 mol), tetrahydro-2,5-dimethoxyfuran (45.7 g, 0.346 mol) and pyridine hydrochloride (1:1) (40 g, 0.346 mol) in dioxane (500 ml) was heated to reflux overnight. The solvent was removed, and the residue was dissolved in EtOAc (100 ml). This solution was washed with brine and H₂O. The separated organic layer was dried (MgSO₄), filtered and the solvent was evaporated to yield 70 g of intermediate 10 which was used as such directly in the next reaction step.

d) Preparation of Intermediate 11

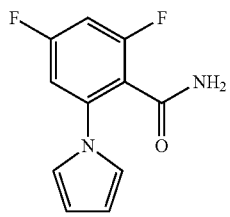 [SMILES: NC(=O)c1c(F)cc(F)cc1-n1cccc1]

NH₃.H₂O (100 ml) was added to a solution of intermediate 10 (70 g (crude), approximately 0.311 mol), HOBT (47 g, 0.346 mol) and EDCI (70 g, 0.346 mol) in DMF (300 ml). The r.m. was stirred overnight. The solvent was removed, and the residue was dissolved in EtOAc. This solution was washed with brine and H₂O. The separated organic layer was dried (MgSO₄), filtered and the solvent was evaporated. Yield: 55 g of intermediate 11 which was used as such directly in the next reaction step.

e) Preparation of Intermediate 12

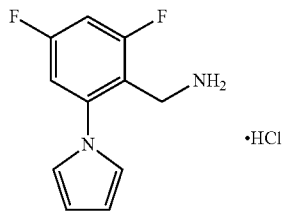 [SMILES: NCc1c(F)cc(F)cc1-n1cccc1 ; Cl]

A 10 M solution of BH₃ in Me₂S (40.5 ml, 0.405 mol) was added to a mixture of intermediate 11 (45 g, 0.2025 mol) in THF (500 ml). The r.m. was refluxed overnight under N₂ atmosphere. Subsequently, 6 N HCl (10 ml) was added while the mixture was cooled on an ice-water bath. The mixture was refluxed again for 30 min, and then solid NaOH was added until pH >9 while the mixture was cooled on an ice-water bath. The mixture was extracted with DCM (2 times 300 ml). The separated organic layer was dried (MgSO$_4$), filtered and the solvent was evaporated. The brown residue was converted to the HCl salt (.HCl) with HCl/2-propanol). Yield: 35 g of intermediate 12 (71% yield).

Example A5 a) Preparation of Intermediate 13

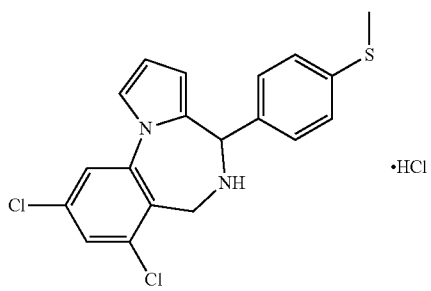 [SMILES: CSc1ccc(C2NCc3c(Cl)cc(Cl)cc3-n3cccc32)cc1 ; Cl]

A mixture of intermediate 3 (2.8 g, 10.0 mmol) and 4-(methylthio)benzaldehyde (1.8 g, 12.0 mmol) in EtOH (15 ml) was refluxed for 4 h. The mixture was cooled and crystallized overnight. The precipitate was filtered off, washed with isopropyl ether and dried in vacuo. Yield: 2.85 g of crude intermediate 13 (.HCl) which was used as such in the next reaction step. If desired, the product can be further purified by HPLC.

b) Preparation of Intermediate 14

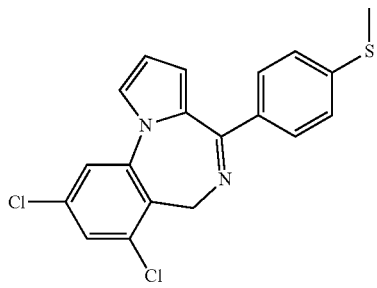 [SMILES: CSc1ccc(C2=NCc3c(Cl)cc(Cl)cc3-n3cccc32)cc1]

Crude intermediate 13 (2.8 g; approximately 6.9 mmol) was neutralized with NH$_3$.H$_2$O (10 ml) and the mixture was extracted with DCM. The separated organic layer was dried (Na$_2$SO$_4$), filtered, and the solvent was evaporated in vacuo. The residue was stirred in DCM (40 ml) and MnO$_2$ (7.2 g, 83.1 mmol) was added to this solution. The r.m. was stirred for 48 h at r.t., and was then filtered over diatomaceous earth (eluent: PE/EtOAc from 5/1 to 2/1). The desired fractions were collected and the solvent was evaporated in vacuo. Yield: 1.60 g of intermediate 14 (62.2% yield).

Example A6 a) Preparation of Intermediate 15

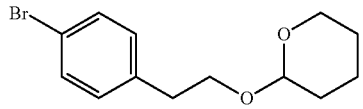 [SMILES: Brc1ccc(CCOC2CCCCO2)cc1]

DHP (7 ml) and PPTS (0.58 g) were added to a solution of 4-bromo-benzeneethanol (9.4 g; 0.0467 mol) in DCM (q.s.) at 25° C. The solution was stirred at 25° C. for 10 hours. The mixture was washed with water (3×50 ml), dried (MgSO$_4$), filtered and the solvent was evaporated. Yield: 12.63 g of intermediate 15 (95% yield).

b) Preparation of Intermediate 16

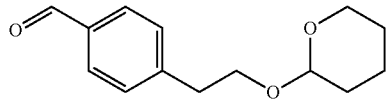 [SMILES: O=Cc1ccc(CCOC2CCCCO2)cc1]

Reaction Under Anhydrous Conditions.

A 2 M solution of n-butyllithium in n-hexane (15 ml) was added dropwise to a solution of intermediate 15 (8.62 g) in THF (150 ml) at −78° C. This mixture was stirred for 1 hour at −78° C. Then DMF (7 ml) was added dropwise, and the reaction mixture was stirred for another 2 hours at −78° C. The reaction mixture was combined with a NH$_4$Cl solution and extracted with EtOAc. The combined organic layers were washed 3 times with a saturated NaCl solution, dried (Na$_2$SO$_4$), filtered and the solvent was evaporated. The purification was carried out by column chromatography over silica gel (eluent: petroleum ether/EtOAc 8/1). The desired fractions were collected and the solvent was evaporated. Yield: 6.57 g of intermediate 16 (94% yield).

Example A7 a) Preparation of Intermediate 17

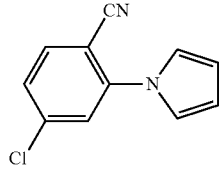 [SMILES: N#Cc1ccc(Cl)cc1-n1cccc1]

2,5-Dimethoxytetrahydrofuran (180 mmol) was added to a mixture of 2-amino-4-chlorobenzonitrile (164 mmol) in HOAc (250 ml). The reaction mixture was stirred at reflux for 30 minutes. The reaction mixture was concentrated under reduced pressure. A saturated aqueous solution of NaHCO$_3$ was added to the concentrate. The mixture was extracted with EtOAc. The combined organic layers were washed with a saturated aqueous solution of NaHCO$_3$ and water, dried over anhydrous Na$_2$SO$_4$, filtered and evaporated. Dark coloured crystals were obtained. The obtained crude was dissolved in DCM and filtered over a silica plug. Yield: Intermediate 17 (99% yield; yellow crystalline solid).

b) Preparation of Intermediate 18

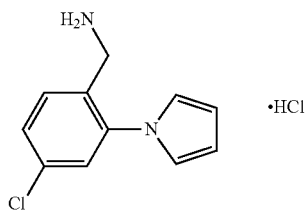 [SMILES: NCc1ccc(Cl)cc1-n1cccc1 ; Cl]

Aluminum(III) lithium hydride (250 mmol) in THF anhydrous (20 ml) was added over 2 minutes to an ice cooled solution of intermediate 17 (114 mmol) in anhydrous THF anhydrous (200 ml). After addition the reaction mixture was stirred for 1 hour. The reaction mixture was added to an ice cooled 15% aqueous solution of potassium sodium 2,3-dihydroxysuccinate tetrahydrate (Rochelle's salt) under vigorously stirring followed by EtOAc (300 ml). The mixture was stirred for 30 min. The layers were separated and the aqueous layer was extracted with EtOAc (300 mL). The combined organic layers were washed with water (50 ml), dried over anhydrous $Na_2SO_4$, filtered and evaporated under reduced pressure to yield a yellow translucent oil.

The obtained oil was dissolved in diethyl ether (800 ml) and HCl in dioxane 4 M (28.5 ml) was added to this solution. The resulting suspension was filtered and washed with diethyl ether. The filter residue was dried at 50° C. to yield intermediate 18 (65% yield; yellow solid).

B. Preparation of the Compounds

Example B1 a) Preparation of Compound 12

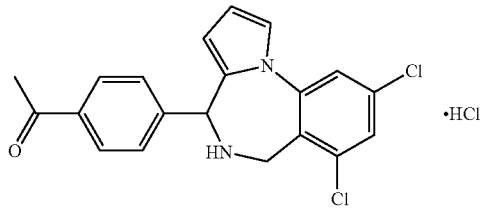 [SMILES: CC(=O)c1ccc(C2NCc3c(Cl)cc(Cl)cc3-n3cccc32)cc1 ; Cl]

A mixture of intermediate 3 (0.552 g, 0.002 mol) and 4-acetyl-benzaldehyde (0.385 g, 0.0026 mol) in EtOH (4 ml) was stirred and refluxed for 3 h. Then, the mixture was cooled and crystallized from the mixture by standing overnight. The product was filtered off and washed (EtOH) and dried. Yield: 0.684 g of compound 12 (84.2% yield).

b) Preparation of Compound 22

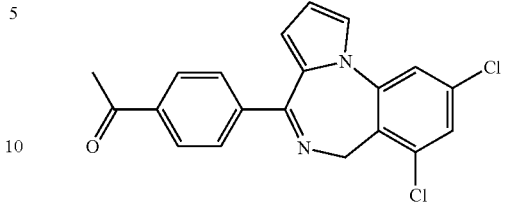

Compound 12 (0.390 g, 0.00096 mol) was stirred in $NH_3.H_2O$ (4 ml). This mixture was extracted with DCM (20 ml). The separated organic layer was dried ($Na_2SO_4$) and filtered. The solution was stirred with $MnO_2$ (2.5 g, 0.028 mol) for 4 days after filtration, and then the solvent was removed. The product was dried in vacuo. Yield: 0.010 g of compound 2 (2.8% yield).

Example B2 a) Preparation of Compound 32

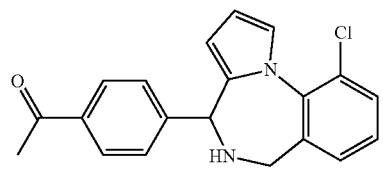 [SMILES: CC(=O)c1ccc(C2NCc3cccc(Cl)c3-n3cccc32)cc1]

A mixture of intermediate 5 (1.5 g, 6.17 mmol) and 4-acetyl-benzaldehyde (1.0 g, 6.78 mmol) in EtOH (10 ml) was refluxed for 4 h. Subsequently, the mixture was left standing overnight at r.t. The solvent was evaporated in vacuo. The residue was purified by preparative HPLC (SEPAX™: 21.2×250 mm; eluent: 10%-40% $CH_3CN$ (0.1% TFA)/$H_2O$ (0.1% TFA); flow rate 25 ml/min; 20 min) The desired fractions were collected and neutralized with a saturated $NaHCO_3$ solution. The mixture was extracted with DCM. The separated organic layer was dried ($Na_2SO_4$), filtered and the solvent was evaporated to yield 0.68 g of compound 31 as an oil (33% yield).

b) Preparation of Compound 15

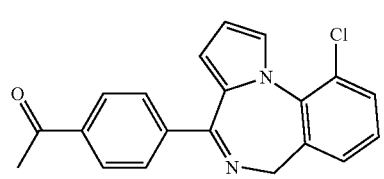 [SMILES: CC(=O)c1ccc(C2=NCc3cccc(Cl)c3-n3cccc32)cc1]

A mixture of compound 32 (0.68 g, 2.02 mmol) and $MnO_2$ (2.63 g, 30.28 mmol) in DCM (20 ml) was stirred for 48 h at r.t. Subsequently, the mixture was filtered over diatomaceous earth, and the filtrate was evaporated in vacuo. The residue was purified by column chromatography (eluent: PE/EtOAc 10/1). The desired fractions were collected and the solvent was evaporated to yield 0.6 g of compound 15 (89% yield).

Example B3 a) Preparation of Compound 8

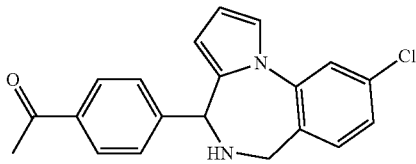 [SMILES: CC(=O)c1ccc(C2NCc3ccc(Cl)cc3-n3cccc32)cc1]

4-Acetyl-benzaldehyde (1.46 g, 9.78 mmol) was added to a solution of intermediate 7 (2.00 g, 8.23 mmol) in EtOH (15 ml). The r.m. was stirred and refluxed for 4 h, and was then cooled. After standing overnight, the precipitate was filtered off and dried in vacuo to yield the crude product. The crude product was purified by HPLC (SEPAX™: 21.2×250 mm; eluent: 35%-55% CH$_3$CN (0.1% TFA)/H$_2$O (0.1% TFA); flow rate 15 ml/min; 25 min) The product fractions were collected and the organic solvent was evaporated. The residue was adjusted to pH 7 with a saturated NaHCO$_3$ solution. DCM (q.s.) was added and the organic layer was separated. The separated organic layer was dried (Na$_2$SO$_4$), filtered and the solvent was evaporated. Yield: 2.1 g of compound 8 (68.4% yield).

b) Preparation of Compound 18

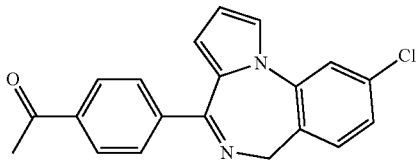 [SMILES: CC(=O)c1ccc(C2=NCc3ccc(Cl)cc3-n3cccc32)cc1]

A solution of compound 8 (2.0 g, 5.9 mmol) and MnO$_2$ (6.1 g, 71.2 mmol) in DCM (50 ml) was stirred at r.t. for 2 days. The mixture was filtered, and the filtrate was concentrated to yield 0.650 g of compound 18 (36.3% yield).

Example B4 a) Preparation of Compound 33

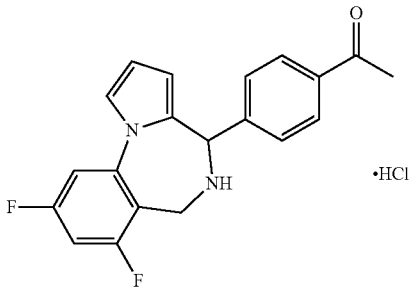 [SMILES: CC(=O)c1ccc(C2NCc3c(F)cc(F)cc3-n3cccc32)cc1 ; Cl]

A mixture of intermediate 12 (1.5 g, 6.13 mmol) and 4-acetylbenzaldehyde (1 g, 6.74 mmol) in EtOH (10 ml) was refluxed for 4 h, and was then left standing overnight at r.t. The precipitate was filtered off, washed with EtOH (q.s.) and dried in vacuo to yield the crude product as an off-white solid. The crude product was purified by HPLC (Synergi™: 50×250 mm; eluent: 10%-40% CH$_3$CN (0.1% TFA)/H$_2$O (0.1% TFA); flow rate 80 ml/min; 25 min). The desired fraction were collected and the solvent was evaporated to yield the trifluoroacetic acid salt. The product was neutralized with a saturated NaHCO$_3$ solution and was extracted with DCM. The separated organic layer was dried, evaporated, and the residue was converted into the HCl salt (1:1) with HCl/dioxane. Yield: 0.7 g of compound 33 (30.5% yield; .HCl).

b) Preparation of Compound 24

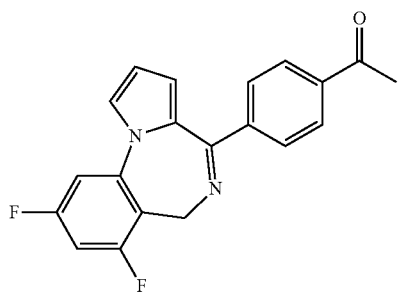 [SMILES: CC(=O)c1ccc(C2=NCc3c(F)cc(F)cc3-n3cccc32)cc1]

Compound 33 (0.6 g, 1.6 mmol) was neutralized with NH$_3$.H$_2$O (10 ml) and was extracted with DCM. The separated organic layer was dried (Na$_2$SO$_4$), filtered and the solvent was evaporated in vacuo. The residue was dissolved in DCM (20 ml), and MnO$_2$ (1.67 g, 19.2 mmol) was added to the solution. The mixture was stirred at r.t. for 48 h. Subsequently, the mixture was filtered over diatomaceous earth. The filtrate was concentrated in vacuo, and the residue was purified by column chromatography (eluent: PE/EtOAc 15/1). The desired fractions were collected and the solvent was evaporated. Yield: 0.37 g of compound 24 (69% yield; white solid).

Example B5 a) Preparation of Compound 5

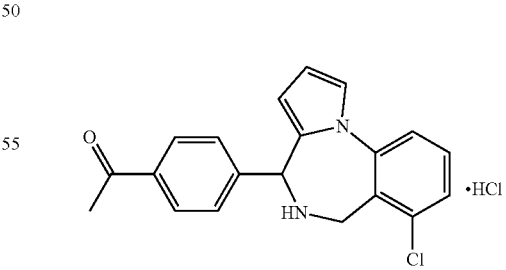

A mixture of 2-chloro-6-(1H-pyrrol-1-yl)benzenemethanamine hydrochloride (1:1) (1.00 g, 0.004 mol; prepared by a protocol analogue to the protocol described for intermediate 3 in A1.c) and 4-acetylbenzaldehyde (0.59 g, 0.004 mol) in EtOH (10 ml) was stirred and refluxed for 2 h. The mixture was crystallized overnight. The precipate was filtered off, washed 3 times with EtOH (5 ml) and dried in vacuo at 80° C. Yield: 0.94 g of compound 5 (63% yield).

b) Preparation of Compound 17

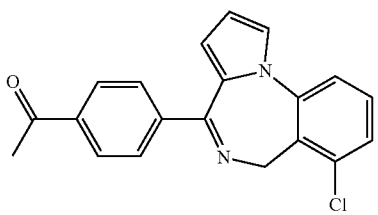 [SMILES: CC(=O)c1ccc(C2=NCc3c(Cl)cccc3-n3cccc32)cc1]

A mixture of H$_2$O (25 ml) and NH$_4$OH (5 ml) was added to a suspension of DCM (50 ml) and compound 5 (0.380 g, 0.97 mmol) at 25° C. The mixture was stirred for 15 min at 25° C. Subsequently, the layers were separated. The separated organic layer was dried (MgSO$_4$), filtered and the solvent was evaporated. The residue was stirred in DCM (50 ml) and MnO$_2$ (0.90 g, 0.01 mol) was added to the solution. The mixture was stirred for 120 h at 25° C. The mixture was filtered over diatomaceous earth and the filtrate was evaporated. The residue was crystallized from EtOH. The product was filtered off and dried. Yield: 0.25 g of compound 17 (75% yield).

Example B6 a) Preparation of Compound 14

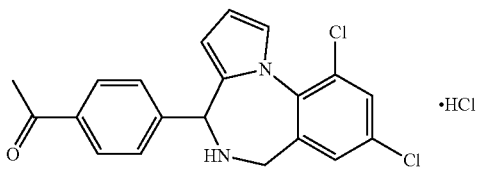 [SMILES: CC(=O)c1ccc(C2NCc3cc(Cl)cc(Cl)c3-n3cccc32)cc1 ; Cl]

A mixture of 3,5-dichloro-2-(1H-pyrrol-1-yl)benzenemethanamine hydrochloride (1:1) (1.86 g, 0.0067 mol; prepared by a protocol analogue to the protocol described for intermediate 3 in A1.c) and 4-acetylbenzaldehyde (0.992 g, 0.0067 mol) in EtOH (20 ml) was stirred and refluxed for 2 h. The mixture was crystallized overnight. The product was filtered off, washed 2 times with EtOH (10 ml) and dried in vacuo at 80° C. Yield: 2.49 g of compound 14 (91% yield; .HCl).

b) Preparation of Compound 26

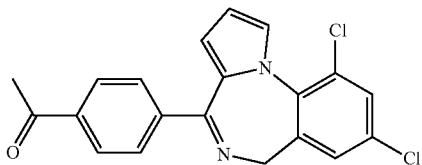 [SMILES: CC(=O)c1ccc(C2=NCc3cc(Cl)cc(Cl)c3-n3cccc32)cc1]

A mixture of compound 14 (0.812 g, 0.002 mol) in DCM (20 ml) was washed with H$_2$O (30 ml), NH$_4$OH (10 ml), and H$_2$O (20 ml). The organic layer was dried (MgSO$_4$) and filtered. MnO$_2$ (1.8 g, 0.02 mol) was added to the filtrate. The mixture was stirred for 96 h at 25° C., and was then filtered over diatomaceous earth. The filtrate was evaporated to yield 0.24 g of compound 26 (33% yield).

Example B7

Preparation of Compound 30

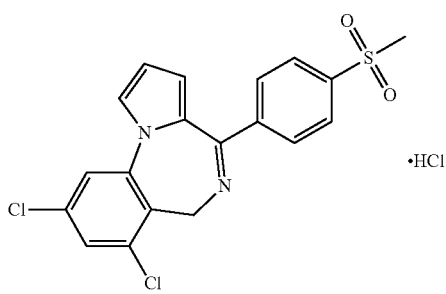 [SMILES: CS(=O)(=O)c1ccc(C2=NCc3c(Cl)cc(Cl)cc3-n3cccc32)cc1 ; Cl]

A solution of oxone (3.3 g, 5.4 mmol) in H$_2$O (10 ml) was added slowly to a mixture of intermediate 14 (1.0 g, 2.7 mmol) in THF (15 ml) at r.t. The r.m. was stirred for 2 h. Subsequently, the mixture was partitioned between DCM and NaHCO$_3$. The organic layer was dried (MgSO$_4$), filtered and the solvent was evaporated to yield a light yellow residue. This residue was purified by column chromatography over silica gel (eluent: PE/EtOAc from 8/1 to 3/1). The desired fractions were collected and the solvent was evaporated in vacuo. Yield: 550 mg of compound 30 (50% yield).

Example B8

Preparation of Compound 1

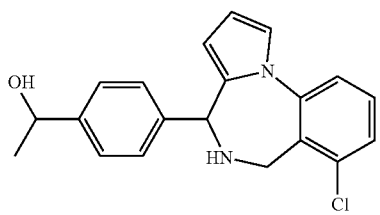 [SMILES: CC(O)c1ccc(C2NCc3c(Cl)cccc3-n3cccc32)cc1]

A mixture of compound 5 (0.372 g, 0.001 mol), DCM (20 ml), NH$_4$OH (5 ml) and H$_2$O (20 ml) were stirred for 15 min at 25° C. The layers were separated. The separated organic layer was washed with H$_2$O (20 ml), dried (MgSO$_4$), and filtered. The filtrate was cooled on ice, and NaBH$_4$ (0.019 g, 0.0005 mol) was added slowly to the cooled r.m. which was stirred at 0° C. for 2 h. Subsequently, H$_2$O (30 ml) was added and the product was extracted with EtOAc. The separated organic layer was dried (MgSO$_4$), filtered, and the solvent was evaporated. The residue was purified by preparative TLC (eluent: DCM/MeOH 30/1). Yield: 0.18 g of compound 1 (53% yield).

Example B9

Preparation of Compound 34

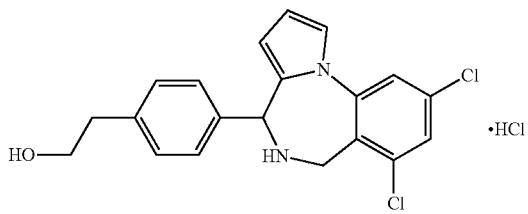 [SMILES: OCCc1ccc(C2NCc3c(Cl)cc(Cl)cc3-n3cccc32)cc1 ; Cl]

A mixture of intermediate 3 (0.552 g; 0.002 mol) and intermediate 16 (0.609 g; 0.0026 mol) in EtOH (10 ml) was stirred and refluxed for 3 hours. Then, the mixture was cooled off and crystallized overnight. The crystals were filtered off and dried to yield 0.410 g of compound 34 (50% yield).

Example B10

Preparation of Compound 39

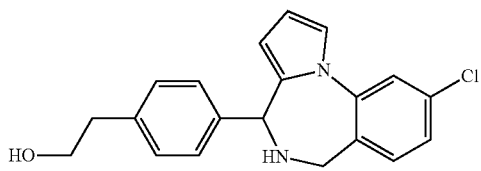 [SMILES: OCCc1ccc(C2NCc3ccc(Cl)cc3-n3cccc32)cc1]

Intermediate 18 was converted to the free amine form through basic extraction to DCM followed by drying over anhydrous $Na_2SO_4$. This free amine of intermediate 18 (5.55 mmol) was added to a mixture of intermediate 16 (4.27 mmol) in anhydrous DCM (100 ml), AcOH (1747 mmol) and an excess of anhydric $Na_2SO_4$. The reaction mixture was stirred for 5 days. Then, the reaction mixture was added to an aqueous solution of $NaHCO_3$ (foaming) until basic. After extraction with DCM, the combined organic layers were dried over anhydrous $Na_2SO_4$, filtered and evaporated under reduced pressure to yield a crude. The obtained crude was purified with flash chromatography (ISOLERA 1—Biotage®) (10% EtOAc in hexane to 100% EtOAc). The desired fractions were collected and the solvent was evaporated. Yield: Compound 39 (2.5% yield).

By using analogous reaction protocols as described in the foregoing examples, the following compounds have been prepared. 'Co. No.' means compound number. 'Pr.' refers to the Example number according to which protocol the compound was synthesized. In case no salt form is indicated, the compound was obtained as a free base.

A compound wherein $R^3$ and $R^4$ are hydrogen, and for which no specific stereochemistry is indicated for a stereocenter in Table 1a or 1b, was obtained as a racemic mixture of R and S enantiomers.

TABLE 1a

| Co. No. | Pr. | $R^1$ | $R^2$ | $R^3$ | $R^4$ | $R^5$ | $R^6$ | Salt Form |
|---|---|---|---|---|---|---|---|---|
| 1 | B8 | 7-Cl | H | H | H | OH-CH(CH₃)- | H | |
| 2 | B8 | 7-Cl | 8-Cl | H | H | OH-CH(CH₃)- | H | •HCl |
| 3 | B8 | 8-Cl | 10-Cl | H | H | OH-CH(CH₃)- | H | •HCl |
| 5 | B5.a | 7-Cl | H | H | H | C(O)CH₃ | H | •HCl |
| 6 | B5.a | 7-Cl | H | H | H | C(O)CH₃ | H | •HBr |
| 8 | B3.a | 9-Cl | H | H | H | C(O)CH₃ | H | |
| 9 | B3.a or B4.a | 7-Cl | 8-Cl | H | H | C(O)CH₃ | H | •HCl |
| 11 | B3.a | 7-Cl | 9-Cl | H | H | C(O)CH₃ | H | |
| 12 | B1.a | 7-Cl | 9-Cl | H | H | C(O)CH₃ | H | •HCl |
| 14 | B6.a | 8-Cl | 10-Cl | H | H | C(O)CH₃ | H | •HCl |
| 32 | B2.a | 10-Cl | H | H | H | C(O)CH₃ | H | |
| 33 | B4.a | 7-F | 9-F | H | H | C(O)CH₃ | H | •HCl |

TABLE 1a-continued

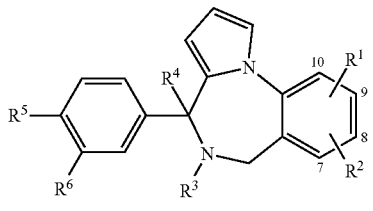

(I-x)

| Co. No. | Pr. | R$^1$ | R$^2$ | R$^3$ | R$^4$ | R$^5$ | R$^6$ | Salt Form |
|---|---|---|---|---|---|---|---|---|
| 34 | B9 | 7-Cl | 9-Cl | H | H | HO—(CH$_2$)$_2$— | H | ·HCl |
| 35 | B9 | 7-Cl | H | H | H | HO—(CH$_2$)$_2$— | H | ·HCl |
| 36 | B9 | 8-Cl | 10-Cl | H | H | HO—(CH$_2$)$_2$— | H | ·HCl |
| 37 | B9 | 7-Cl | 8-Cl | H | H | HO—(CH$_2$)$_2$— | H | ·HCl |
| 38 | B9 | 7-Cl | 10-Cl | H | H | HO—(CH$_2$)$_2$— | H | ·HCl |
| 39 | B10 | 9-Cl | H | H | H | HO—(CH$_2$)$_2$— | H | |
| 40 | B1.a | 7-F | H | H | H | H$_3$C—C(=O)— | H | ·HCl |
| 41 | B1.a | 7-Cl | 10-Cl | H | H | H$_3$C—C(=O)— | H | ·HCl |
| 15 | B2.b | 10-Cl | H | bond | | H$_3$C—C(=O)— | H | |
| 17 | B5.b | 7-Cl | H | bond | | H$_3$C—C(=O)— | H | |
| 18 | B3.b | 9-Cl | H | bond | | H$_3$C—C(=O)— | H | |
| 20 | B3.b or B1.b | 7-F | H | bond | | H$_3$C—C(=O)— | H | |
| 21 | B3.b or B1.b | 7-Cl | 8-Cl | bond | | H$_3$C—C(=O)— | H | ·HCl |
| 22 | B1.b | 7-Cl | 9-Cl | bond | | H$_3$C—C(=O)— | H | |
| 24 | B4.b | 7-F | 9-F | bond | | H$_3$C—C(=O)— | H | |
| 25 | B1.b | 7-Cl | 10-Cl | bond | | H$_3$C—C(=O)— | H | |

TABLE 1a-continued

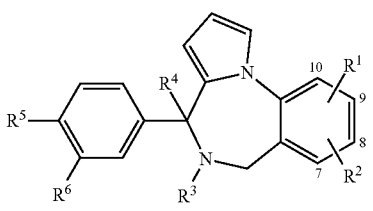

(I-x)

| Co. No. | Pr. | R$^1$ | R$^2$ | R$^3$ | R$^4$ | R$^5$ | R$^6$ | Salt Form |
|---|---|---|---|---|---|---|---|---|
| 26 | B6.b | 8-Cl | 10-Cl | bond | | H$_3$C—C(=O)— | H | |
| 28 | B7 | 7-Cl | H | bond | | H$_3$C—S(=O)$_2$— | H | |
| 29 | B7 | 7-F | H | bond | | H$_3$C—S(=O)$_2$— | H | |
| 30 | B7 | 7-Cl | 9-Cl | bond | | H$_3$C—S(=O)$_2$— | H | |

TABLE 1b (I-y)

| Co. No. | Pr. | R$^1$ | R$^2$ | R$^3$ | R$^4$ | R$^6$ | R$^5$ | Salt Form |
|---|---|---|---|---|---|---|---|---|
| 4 | B3.a | 7-Cl | H | H | H | H | H$_3$C—C(=O)— | |
| 7 | B4.a | 7-Cl | H | H | H | F | H$_3$C—C(=O)— | ·HCl |
| 10 | B4.a | 7-Cl | 9-Cl | H | H | H | H$_3$C—C(=O)— | ·HCl |
| 13 | B3.a | 7-Cl | 9-Cl | H | H | F | H$_3$C—C(=O)— | |

TABLE 1b-continued (I-y)

| Co. No. | Pr. | R¹ | R² | R³ | R⁴ | R⁶ | R⁵ | Salt Form |
|---|---|---|---|---|---|---|---|---|
| 16 | B4.b | 7-Cl | H | bond | | H | C(=O)CH₃ | |
| 19 | B4.b | 7-Cl | H | bond | | F | C(=O)CH₃ | |
| 23 | B4.b | 7-Cl | 9-Cl | bond | | F | C(=O)CH₃ | |
| 27 | B7 | 7-Cl | H | bond | | H | S(=O)₂CH₃ | |
| 31 | B7 | 7-Cl | 9-Cl | bond | | H | S(=O)₂CH₃ | |

Analytical Results

LCMS—General Procedure

The HPLC measurement was performed using an Agilent 1100 module comprising a pump, a diode-array detector (DAD) (wavelength used 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive and 3000 V for negative ionization mode. Fragmentation voltage was 50 V. Drying gas temperature was maintained at 350° C. at a flow of 10 l/min.

LCMS Method 1

In addition to the general procedure: Reversed phase HPLC was carried out on a YMC-Pack ODS-AQ, 50×2.0 mm 5 μm column with a flow rate of 0.8 ml/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 μl were used. Oven temperature was 50° C. (MS polarity: positive)

LCMS Method 2

In addition to the general procedure: Reversed phase HPLC was carried out on a YMC-Pack ODS-AQ, 50×2.0 mm 5 μm column with a flow rate of 0.8 ml/min. 2 mobile phases (mobile phase A: water with 0.1% TFA; mobile phase B: CH₃CN with 0.05% TFA) were used. First, 90% A and 10% B was hold for 0.8 min. Then a gradient was applied to 20% A and 80% B in 3.7 min and hold for 3 min. Typical injection volumes of 2 μl were used. Oven temperature was 50° C. (MS polarity: positive)

Melting Points

For a number of compounds, melting points (m.p.) were determined with a WRS-2A melting point apparatus purchased from Shanghai Precision and Scientific Instrument Co. Ltd. Melting points were measured with a linear heating up rate of 0.2-5.0° C./min The reported values are melt ranges. The maximum temperature was 300° C.

The results of the analytical measurements are shown in table 2.

TABLE 2

Retention time ($R_t$) in min., $[M + H]^+$ peak (protonated molecule), and m.p. (melting point in ° C.).

| Co. No. | $R_t$ | $[M + H]^+$ | LCMS Method | m.p. (° C.) |
|---|---|---|---|---|
| 1 | 3.02 | 339 | 2 | 118.5-121.2 |
| 2 | 4.33 | 373 | 1 | 215.3-216.7 |
| 3 | 3.58 | 373 | 2 | n.d. |
| 4 | 3.30 | 337 | 2 | dec |
| 5 | 3.07 | 337 | 2 | dec |
| 6 | n.d. | n.d. | — | n.d. |
| 7 | 4.32 | 355 | 1 | 174.3-176.0 |
| 8 | 3.44 | 337 | 2 | 185.4-186.9 |
| 9 | 3.36 | 371 | 2 | 253.3-256.1 |
| 10 | 3.63 | 371 | 2 | 274.2-274.3 |
| 11 | 3.70 | 371 | 2 | 204.8-206.6 |
| 12 | 3.42 | 371 | 2 | dec |
| 13 | 3.52 | 389 | 2 | n.d. |
| 14 | 3.63 | 371 | 2 | 259.3-264.5 |
| 15 | 3.21 | 335 | 2 | 171.4-171.8 |
| 16 | 3.24 | 335 | 2 | n.d. |
| 17 | 3.05 | 335 | 2 | 252.3-252.6 |
| 18 | 3.18 | 335 | 2 | 114.4-115.7 |
| 19 | 3.07 | 353 | 2 | 146.2-147.7 |
| 20 | 3.91 | 319 | 1 | 215.2-216.0 |
| 21 | 3.16 | 369 | 2 | 209.2-212.3 |
| 22 | 3.62 | 369 | 2 | 250.2-254.2 |
| 23 | 3.41 | 387 | 2 | 192.3-193.4 |
| 24 | 3.98 | 337 | 1 | 226.9-230.0 |
| 25 | 3.49 | 369 | 2 | n.d. |
| 26 | 3.58 | 369 | 2 | 183.6-186.7 |
| 27 | 4.05 | 371 | 1 | 189.8-191.0 |
| 28 | 4.00 | 371 | 1 | 218.5-219.9 |
| 29 | 3.83 | 355 | 1 | 92.0-95.0 |
| 30 | 3.20 | 405 | 2 | n.d. |
| 31 | 3.29 | 405 | 2 | 221.2-221.5 |
| 32 | n.d. | n.d. | — | — |
| 33 | n.d. | n.d. | — | dec |
| 34 | 3.48 | 373 | 2 | — |
| 35 | 4.27 | 339 | 1 | 237.3-239.9 |
| 36 | 3.61 | 373 | 2 | 248.7-250.3 |

TABLE 2-continued

Retention time ($R_t$) in min., $[M + H]^+$ peak (protonated molecule), and m.p. (melting point in ° C.).

| Co. No. | $R_t$ | $[M + H]^+$ | LCMS Method | m.p. (° C.) |
|---|---|---|---|---|
| 37 | 3.37 | 373 | 2 | 244.9-245.5 |
| 38 | 3.36 | 373 | 2 | 236.3-237.9 |

("n.d." means not determined; "dec" means decomposed).

$^1$H NMR For a number of compounds, $^1$H NMR spectra were recorded on a Bruker DPX-300, or on a Bruker DPX-400 spectrometer with standard pulse sequences, operating at 300 MHz and 400 MHz respectively, using CHLOROFORM-d (deuterated chloroform, CDCl$_3$) or DMSO-d$_6$ (deuterated DMSO, dimethyl-d6 sulfoxide) as solvents. Chemical shifts (δ) are reported in parts per million (ppm) relative to tetramethylsilane (TMS), which was used as internal standard.

Compound 1: $^1$H NMR (300 MHz, DMSO-d$_6$) δ ppm 1.30 (d, J = 6.4 Hz, 3H), 3.52 (d, J = 13.5 Hz, 1H), 4.22 (d, J = 13.5 Hz, 1H), 4.65-4.76 (m, 2H), 5.10 (d, J = 4.2 Hz, 1H), 5.34-5.39 (m, 1H), 6.11 (t, J = 3.2 Hz, 1H), 7.12 (dd, J = 3.0, 1.5 Hz, 1H), 7.26 (d, J = 8.0 Hz, 2H), 7.36 (d, J = 7.9 Hz, 2H), 7.41-7.48 (m, 3H).

Compound 5: $^1$H NMR (400 MHz, DMSO-d$_6$) δ ppm 2.63 (s, 3H), 3.88 (br. d, J = 14.1 Hz, 1H), 4.59 (d, J = 13.8 Hz, 1H), 5.39 (s, 1H), 5.83 (s, 1H), 6.30 (s, 1H), 7.44 (s, 1H), 7.60-7.74 (m, 3H), 7.92 (d, J = 8.0 Hz, 2H), 8.06 (d, J = 8.0 Hz, 2H), 10.58 (br. s, 1H), 10.45 (br. s, 1H).

Compound 15: $^1$H NMR (300 MHz, DMSO-d$_6$) δ ppm 2.60 (s, 3H), 4.12 (d, J = 10.9 Hz, 1H), 4.92 (d, J = 11.0 Hz, 1H), 6.46 (dd, J = 3.8, 2.8 Hz, 1H), 6.49 (dd, J = 3.8, 1.7 Hz, 1H), 7.39 (t, J = 7.8 Hz, 1H), 7.62 (d, J = 7.8 Hz, 2H), 7.70 (dd, J = 2.8, 1.6 Hz, 1H), 7.83 (d, J = 8.3 Hz, 1H), 7.99 (d, J = 8.5 Hz, 2H).

Compound 16: $^1$H NMR (300 MHz, CHLOROFORM-d) δ ppm 2.56 (s, 3H), 4.14 (br. s, 1H), 5.47 (br. s, 1H), 6.35-6.49 (m, 2H), 7.15-7.36 (m, 4H), 7.41 (t, J = 7.7 Hz, 1H), 7.87 (d, J = 7.7 Hz, 1H), 7.97 (d, J = 7.8 Hz, 1H), 8.22 (s, 1H).

Compound 17: $^1$H NMR (300 MHz, CHLOROFORM-d) δ ppm 2.63 (s, 3 H) 4.23 (br. s., 1 H) 5.53 (br. s., 1 H) 6.33-6.60 (m, 2 H) 7.28-7.44 (m, 4 H) 7.72-7.90 (m, 2 H) 7.89-8.10 (m, 2 H).

Compound 18: $^1$H NMR (400 MHz, CHLOROFORM-d) δ ppm 2.64 (s, 3H), 4.71 (br. s, 2H), 6.49-6.54 (m, 1H), 6.54-6.61 (m, 1H), 7.32 (d, J = 8.1 Hz, 1H), 7.41 (s, 1H), 7.45 (s, 1H), 7.48 (d, J = 8.1 Hz, 1H), 7.81 (d, J = 8.0 Hz, 2H), 7.98 (d, J = 8.0 Hz, 2H).

Compound 19: $^1$H NMR (400 MHz, CHLOROFORM-d) δ ppm 2.65 (d, J = 4.7 Hz, 3H), 4.16 (br. s, 1H), 5.51 (br. s, 1H), 6.46 (s, 2H), 7.16 (dd, J = 10.6, 8.6 Hz, 1H), 7.28-7.43 (m, 4H), 7.93-8.03 (m, 1H), 8.17 (dd, J = 7.2, 2.4 Hz, 1H).

Compound 20: $^1$H NMR (400 MHz, CHLOROFORM-d) δ ppm 2.63 (s, 3 H) 4.69 (br. s., 2 H) 6.39-6.54 (m, 2 H) 7.09 (t, J = 8.5 Hz, 1 H) 7.19 (d, J = 8.0 Hz, 1 H) 7.30-7.43 (m, 2 H) 7.81 (m, J = 8.3 Hz, 2 H) 7.96 (m, J = 8.3 Hz, 2 H).

Compound 21: $^1$H NMR (400 MHz, CHLOROFORM-d/at 0 degrees!) δ ppm 2.65 (s, 3 H), 4.23 (br. d, J = 11.4 Hz, 1 H), 5.60 (br. d, J = 11.4 Hz, 1 H), 6.47-6.51 (m, 2 H), 7.25 (d, J = 8.6 Hz, 1 H), 7.36 (t, J = 2.2 Hz, 1 H), 7.51 (d, J = 8.6 Hz, 1 H), 7.81 (d, J = 8.3 Hz, 2 H), 7.96 (d, J = 8.4 Hz, 2 H).

Compound 22: $^1$H NMR (400 MHz, CHLOROFORM-d) δ ppm 2.63 (s, 3H), 4.17 (br. s, 1H), 5.50 (br. s, 1H), 6.43-6.56 (m, 2H), 7.30 (s, 1H), 7.35 (s, 1H), 7.42 (s, 1H), 7.80 (d, J = 8.0 Hz, 2H), 7.96 (d, J = 8.0 Hz, 2H).

Compound 23: $^1$H NMR (300 MHz, CHLOROFORM-d) δ ppm 2.65 (d, J = 4.7 Hz, 3 H) 4.13 (br. s., 1 H) 5.45 (br. s., 1 H) 6.47 (m, J = 2.3 Hz, 2 H) 7.17 (dd, J = 10.5, 8.7 Hz, 1 H) 7.30 (d, J = 1.9 Hz, 1 H) 7.35 (t, J = 2.2 Hz, 1 H) 7.41 (d, J = 1.9 Hz, 1 H) 7.83-8.02 (m, 1 H) 8.16 (dd, J = 7.1, 2.4 Hz, 1 H).

Compound 24: $^1$H NMR (400 MHz, CHLOROFORM-d) δ ppm 2.64 (s, 3 H) 4.72 (br. s., 2 H) 6.49 (m, J = 2.3 Hz, 2 H) 6.85 (td, J = 8.9, 2.3 Hz, 1 H) 6.96 (d, J = 9.0 Hz, 1 H) 7.35 (t, J = 2.0 Hz, 1 H) 7.80 (m, J = 8.3 Hz, 2 H) 7.96 (m, J = 8.3 Hz, 2 H).

Compound 25: $^1$H NMR (400 MHz, CHLOROFORM-d) δ ppm 2.64 (s, 3H) 4.11 (d, J = 11.5 Hz, 1 H) 5.52 (d, J = 9.3 Hz, 1 H) 6.35-6.64 (m, 2 H) 7.35-7.48 (m, 2 H) 7.54-7.68 (m, 1 H) 7.85-8.09 (m, 4 H).

Compound 26: $^1$H NMR (400 MHz, DMSO-d$_6$) δ ppm 2.60 (s, 3H), 4.10 (d, J = 11.0 Hz, 1H), 4.94 (d, J = 11.0 Hz, 1H), 6.45-6.53 (m, 2H), 7.71 (br. s, 1H), 7.77-7.88 (m, 4H), 7.99 (d, J = 8.1 Hz, 2H).

Compound 27: $^1$H NMR (300 MHz, CHLOROFORM-d) δ ppm 3.06 (s, 3 H) 4.21 (br. s., 1 H) 5.55 (br. s., 1 H) 6.49 (br. s., 2 H) 7.28-7.47 (m, 4 H) 7.61 (t, J = 7.7 Hz, 1 H) 7.97-8.13 (m, 2 H) 8.29 (s, 1 H).

Compound 28: $^1$H NMR (300 MHz, DMSO-d$_6$) δ ppm 3.25 (s, 3 H) 4.16 (br. s., 1 H) 5.32 (br. s., 1 H) 6.54 (m, J = 2.3 Hz, 2 H) 7.38-7.60 (m, 3 H) 7.79 (t, J = 2.2 Hz, 1 H) 7.83-7.93 (m, 2 H) 7.93-8.00 (m, 2 H).

Compound 29: $^1$H NMR (300 MHz, CHLOROFORM-d) δ ppm 3.06 (s, 3H), 4.81 (br. s, 2H), 6.48-6.57 (m, 2H), 7.12 (t, J = 8.5 Hz, 1H), 7.19 (d, J = 8.1 Hz, 1H), 7.38 (td, J = 8.3, 5.8 Hz, 1H), 7.45 (t, J = 2.3 Hz, 1H), 7.90-8.02 (m, 4H).

Compound 30: $^1$H NMR (300 MHz, CHLOROFORM-d) δ ppm 3.06 (s, 3 H) 4.19 (br. s., 1 H) 5.50 (br. s., 1 H) 6.38-6.60 (m, 2 H) 7.30 (d, J = 1.9 Hz, 1 H) 7.35-7.40 (m, 1 H) 7.43 (d, J = 1.9 Hz, 1 H) 7.84-8.04 (m, 4 H).

Compound 31: $^1$H NMR (300 MHz, CHLOROFORM-d) δ ppm 3.05 (s, 3 H) 4.17 (br. s., 1 H) 5.49 (br. s., 1 H) 6.36-6.58 (m, 2 H) 7.31 (d, J = 1.9 Hz, 1 H) 7.35-7.40 (m, 1 H) 7.42 (d, J = 1.9 Hz, 1 H) 7.60 (t, J = 7.7 Hz, 1 H) 8.03 (m, J = 7.7 Hz, 2 H) 8.27 (s, 1 H).

Compound 34: $^1$H NMR (400 MHz, DMSO-d$_6$) δ ppm 2.75 (t, J = 6.8 Hz, 2 H) 3.61 (t, J = 6.8 Hz, 2 H) 3.81 (d, J = 14.3 Hz, 1 H) 4.53 (d, J = 14.1 Hz, 1 H) 4.65 (br. s., 1 H) 5.29 (br. s., 1H) 5.87 (br. s., 1 H) 6.28 (br. s., 1 H) 7.33 (d, J = 7.8 Hz, 2 H) 7.46 (br. s., 1 H) 7.56 (d, J = 7.8 Hz, 2 H) 7.78 (s, 1 H) 7.83 (s, 1 H) 9.66 (br. s., 1 H) 10.38 (br. s., 1 H).

Compound 35: $^1$H NMR (400 MHz, DMSO-d$_6$) δ ppm 2.76 (t, J = 6.8 Hz, 2 H) 3.62 (t, J = 6.9 Hz, 2 H) 3.84 (d, J = 12.5 Hz, 1 H) 4.53 (d, J = 14.1 Hz, 1 H) 4.67 (br. s., 1 H) 5.17 (br. s., 1 H) 5.84 (br. s., 1 H) 6.28 (t, J = 3.1 Hz, 1 H) 7.32 (d, J = 8.0 Hz, 2 H) 7.39 (br. s., 1 H) 7.56-7.74 (m, 5 H) 10.13 (br. s., 1 H) 10.42 (br. s., 1 H).

Compound 36: $^1$H NMR (300 MHz, DMSO-d$_6$) δ ppm 2.76 (t, J = 6.8 Hz, 2 H) 3.51-3.69 (m, 3 H) 4.36 (d, J = 13.9 Hz, 1 H) 4.67 (br. s., 1 H) 5.26 (br. s., 1 H) 5.91 (d, J = 3.8 Hz, 1 H) 6.28 (t, J = 3.4 Hz, 1 H) 7.33 (m, J = 7.9 Hz, 2 H) 7.38 (dd, J = 3.0, 1.5 Hz, 1 H) 7.63 (m, J = 7.9 Hz, 2 H) 7.78 (d, J = 2.3 Hz, 1 H) 8.06 (d, J = 2.3 Hz, 1 H) 9.77 (br. s., 1 H) 10.31 (br. s., 1 H).

Compound 37: $^1$H NMR (300 MHz, DMSO-d$_6$) δ ppm 2.76 (t, J = 6.8 Hz, 2 H) 3.62 (t, J = 7.0 Hz, 2 H) 3.88 (d, J = 13.9 Hz, 1 H) 4.58 (d, J = 13.9 Hz, 1 H) 5.25 (br. s., 1 H) 5.86 (d, J = 3.4 Hz, 1 H) 6.29 (t, J = 3.4 Hz, 1 H) 7.33 (d, J = 8.3 Hz, 2 H) 7.41 (dd, J = 2.8, 1.7 Hz, 1 H) 7.59-7.68 (m, 3 H) 7.96 (d, J = 9.0 Hz, 1 H) 10.15 (br. s., 1 H) 10.44 (br. s., 1 H).

The $^1$H NMR spectrum of compound 39 was recorded on a 400 MHz Bruker Avance III nanobay spectrometer: (DMSO-d6) δ ppm 2.71 (t, J = 8 Hz, 2H), 3.48 (s, 1H), 3.57 (dt, J = 8 Hz, 4 Hz, 2H), 3.86 (d, J = 12 Hz, 1H), 4.65 (t, J = 4 Hz, 1H), 4.71 (s, 1H), 5.36 (m, 1H), 6.10 (t, J = 4 Hz, 1H), 7.16 (d, J = 8 Hz, 2H), 7.17 (m, 1H), 7.33 (d, J = 8.3 Hz, 2 H) 7.41 (dd, J = 2.8, 1.7 Hz, 1 H) 7.39 (dd, J = 8 Hz, 2 Hz, 1H), 7.42 (d, J = 8 Hz, 1H), 7.57 (d, J = 2 Hz, 1H).

D. Pharmacological Examples

Example D.1

Measurement of Antifungal Activity In Vitro

The standard susceptibility screen was performed in 96-well plates (U-bottom, Greiner Bio-One). Serial dilutions (2-fold or 4-fold) of 20 mM compound stock solutions were made in 100% DMSO, followed by an intermediate dilution step in water. These serial dilutions (10 nl) were then spotted onto test-plates that could be stored in the dark at 4° C. for a maximum period of 2 weeks. An adequate broad dose-range was included with 64 µM as the highest in-test concentration. The culture medium RPMI-1640 was supplemented with L-glutamine, 2% glucose and buffered with 3-(N-morpholino)-propanesulfonic acid (MOPS) at pH 7.0±0.1.

The different fungal species/isolates (Table 3a) were cryo-preserved and 1/1000 diluted in medium just prior to use. A standard inoculum of 200 µl containing $10^3$ colony-forming unit (cfu) was then added to each well. A positive control (100% growth=fungal culture without antifungal) and a negative control (0% growth =RPMI-MOPS medium) were included on each plate. Optimal incubation time and temperature were dependent on the fungal species and varied from 24 h for yeasts (37° C.) to one week or more for dermatophytes (27° C.) Inhibition of fungal growth was measured after adding 10 µl of 0.005% (w/v) resazurin (Sigma Aldrich) to each well, based on the principle that living cells convert the non-fluorescent blue resazurin into the pink and fluorescent resorufin, allowing fluorimetric reading ($\lambda_{ex}$ 550 nm and $\lambda_{em}$ 590 nm) after an additional incubation period ('resa' time mentioned in Table 3a). Results are shown in Table 3b as $pIC_{50}$ values.

TABLE 3a

Incubation conditions for the different fungal species.

| Species | Temperature (° C.) | Time | Resa time |
|---|---|---|---|
| Microsporum canis | 27 | 9 days | 24 hours |
| Trichophyton mentagrophytes | 27 | 7 days | 24 hours |
| Trichophyton rubrum | 27 | 7 days | 24 hours |
| Scedosporium apiospermum | 37 | 48 hours | 17 hours |
| Scedosporium prolificans | 37 | 48 hours | 17 hours |
| Sporothrix schenkii | 27 | 4 days | 24 hours |
| Aspergillus fumigatus | 27 | 48 hours | 17 hours |
| Candida parapsilosis | 37 | 24 hours | 4 hours |
| Cryptococcus neoformans | 37 | 24 hours | 4 hours |
| Rhizopus oryzae | 37 | 24 hours | 6 hours |
| Rhizomucor miehei | 37 | 48 hours | 17 hours |
| Mucor circinelloides | 27 | 48 hours | 17 hours |

'Resa time' represents the additional incubation time after the addition of resazurin to the test system.

TABLE 3b

Activities of the test compounds in vitro

| Co. No. | Inf. A | Inf. B | Inf. C | Inf. D | Inf. E | Inf. F | Inf. G | Inf. H | Inf. I | Inf. J | Inf. K |
|---|---|---|---|---|---|---|---|---|---|---|---|
| 5 | 4.4 | 6.1 | 6.3 | 5.1 | 5.7 | 4.6 | 6.2 | n.d. | n.d. | n.d. | n.d. |
| 6 | 4.7 | 6.2 | 6.4 | <4.2 | 4.5 | <4.2 | n.d. | n.d. | n.d. | n.d. | n.d. |
| 17 | <4.5 | 6.7 | 7.4 | <4.5 | <4.5 | <4.5 | 6.6 | <4.2 | <4.2 | <4.2 | <4.2 |
| 9 | 5.0 | 5.6 | 5.7 | <4.2 | <4.2 | 4.5 | 4.5 | n.d. | n.d. | n.d. | n.d. |
| 14 | 4.6 | 5.6 | 6.2 | <4.2 | <4.2 | 4.3 | 4.6 | n.d. | n.d. | n.d. | n.d. |
| 26 | 5.9 | 6.2 | 7.1 | <4.2 | 5.8 | 5.0 | 5.4 | n.d. | n.d. | n.d. | n.d. |
| 1 | <4.2 | 5.5 | 5.5 | <4.2 | <4.2 | 4.2 | 4.9 | n.d. | n.d. | n.d. | n.d. |
| 21 | <4.2 | <4.2 | <4.2 | <4.2 | <4.2 | <4.2 | <4.2 | n.d. | n.d. | n.d. | n.d. |
| 2 | <4.2 | 4.7 | <4.2 | <4.2 | <4.2 | <4.2 | <4.2 | n.d. | n.d. | n.d. | n.d. |
| 3 | <4.2 | 5.0 | 6 | <4.2 | <4.2 | 4.7 | 4.4 | n.d. | n.d. | n.d. | n.d. |
| 4 | <4.2 | 5.0 | 5.3 | <4.2 | <4.2 | <4.2 | 4.6 | n.d. | n.d. | n.d. | n.d. |
| 11 | 4.3 | 6.0 | 5.7 | <4.2 | <4.2 | 5.2 | 5.3 | n.d. | n.d. | n.d. | n.d. |
| 12 | <4.2 | 4.9 | 5.7 | <4.2 | <4.2 | <4.2 | 5.1 | n.d. | n.d. | n.d. | n.d. |
| 10 | <4.2 | 5.3 | 5.7 | <4.2 | <4.2 | <4.2 | 5.2 | n.d. | n.d. | n.d. | n.d. |
| 22 | 5.4 | 7.0 | 7.3 | 4.6 | 6.6 | 5.0 | 6.5 | 4.3 | 5.9 | <4.2 | <4.2 |
| 16 | 4.6 | 6.5 | 7.3 | <4.2 | 6.2 | <4.2 | 6.4 | <4.2 | <4.2 | <4.2 | <4.2 |
| 25 | <4.2 | 5.5 | 5.3 | <4.2 | <4.2 | <4.2 | 5.0 | n.d. | n.d. | n.d. | n.d. |
| 27 | <4.2 | 5.2 | 5.1 | <4.2 | <4.2 | 4.2 | 5.1 | n.d. | n.d. | n.d. | n.d. |
| 31 | <4.2 | <4.2 | <4.2 | <4.2 | <4.2 | <4.2 | <4.2 | n.d. | n.d. | n.d. | n.d. |
| 29 | <4.2 | 5.0 | 5.6 | <4.2 | 4.3 | 4.5 | 5.2 | n.d. | n.d. | n.d. | n.d. |
| 28 | <4.2 | 5.9 | 5.7 | <4.2 | <4.2 | <4.2 | 5.6 | <4.2 | 5.1 | <4.2 | <4.2 |
| 13 | <4.2 | 5.1 | 5.7 | <4.2 | <4.2 | <4.2 | <4.2 | n.d. | n.d. | n.d. | n.d. |
| 30 | 4.3 | 5.4 | 5.7 | <4.2 | 4.2 | 4.8 | 5.2 | n.d. | n.d. | n.d. | n.d. |
| 8 | 4.5 | <4.2 | 5.7 | <4.2 | 4.9 | 4.3 | 5.3 | n.d. | n.d. | n.d. | n.d. |
| 7 | <4.2 | 5.1 | 6.0 | <4.2 | <4.2 | <4.2 | 5.2 | n.d. | n.d. | n.d. | n.d. |
| 23 | <4.2 | <4.2 | <4.2 | <4.2 | <4.2 | <4.2 | <4.2 | n.d. | n.d. | n.d. | n.d. |
| 15 | 5.8 | 6.2 | 6.9 | <4.2 | 6.3 | 5.7 | 6.4 | 5.0 | 5.7 | <4.2 | 5.1 |
| 19 | <4.2 | 5.8 | 6.7 | <4.2 | 5.7 | <4.2 | 6.1 | <4.2 | 5.9 | <4.2 | <4.2 |
| 18 | 5.1 | 5.7 | 6.5 | 4.2 | 6.3 | 5.8 | 6.0 | 4.4 | 4.9 | <4.2 | <4.2 |
| 24 | 4.7 | 5.7 | 6.9 | 5.4 | 6.1 | 5.0 | 6.2 | 5.1 | 5.6 | <4.2 | <4.2 |
| 20 | <4.2 | 5.9 | 7.0 | <4.2 | 6.3 | <4.2 | 6.4 | <4.2 | 6.2 | <4.2 | <4.2 |
| 34 | <4.2 | 5.7 | 4.9 | <4.2 | <4.2 | 4.5 | 4.7 | n.d. | n.d. | n.d. | n.d. |
| 35 | <4.2 | 4.4 | 5.1 | <4.2 | <4.2 | 4.3 | 4.9 | n.d. | n.d. | n.d. | n.d. |
| 36 | <4.2 | 4.3 | 4.5 | <4.2 | <4.2 | 4.6 | 4.7 | n.d. | n.d. | n.d. | n.d. |
| 37 | 4.8 | <4.2 | 4.5 | <4.2 | 4.4 | 5.0 | 4.4 | n.d. | n.d. | n.d. | n.d. |
| 38 | <4.2 | 5.7 | 5.1 | <4.2 | <4.2 | 4.7 | 4.7 | n.d. | n.d. | n.d. | n.d. |

('n.d.' means not determined; 'Inf.' means infection; values are pIC$_{50}$ values)
Inf. 'A': *Sporothrix schenkii* B62482
Inf. 'B': *Microsporum canis* B68128
Inf. 'C': *Trichophyton rubrum* B68183
Inf. 'D': *Candida parapsilosis* B66126
Inf. 'E': *Aspergillus fumigatus* B42928
Inf. 'F': *Cryptococcus neoformans* B66663
Inf. 'G': *Trichophyton mentagrophytes* B70554
Inf. 'H': *Scedosporium apiospermum* IHEM3817
Inf. 'I': *Scedosporium prolificans* IHEM21157
Inf. 'J': *Rhizopus oryzae* IHEM5223
Inf. 'K': *Rhizomucor miehei* IHEM13391
Inf. 'L': *Mucor circinelloides* IHEM21105
The pIC$_{50}$ values for Inf. 'L' were determined for compounds 15, 16, 18, 19, 20, 22, 24, and 28, and were <4.2.

Example D.2

Liver Metabolic Stability Assay

Liver preparations (microsomal fractions) were obtained from BD Gentest (San Jose, Calif., US). Metabolic stability was assessed using the following assay conditions. All incubations were conducted by shaking reaction mixtures (250 μl) containing 1 mg of microsomal protein preparation/ml, NADPH-generating system ("NADPH" means β-nicotinamide adenine dinucleotide phosphate, reduced) (0.1 mM NADP, 5.0 mM $MgCl_2$, 1.65 mM glucose-6-phosphate and 0.125 U glucose-6-phosphate dehydrogenase), and 0.5 M Na-K-phosphate buffer (pH 7.4). The mixture was pre-incubated at 37° C. for 5 min and the enzymatic reaction was started by addition of 5 μM test compound. After 0 (control) and 15 minutes (min), the reactions were terminated by addition of DMSO (500 μl). The precipitated material was removed by centrifugation at 1200 g for 10 min. The supernatant was analysed by LC-MS/MS on a ThermoFinnigan LCQ Deca XP ion-trap mass spectrometer equipped with an atmospheric pressure chemical ionisation source. Calculation of %-compound remaining was as described by Kantharaj et al. 2003 ((Kantharaj E., Tuytelaars A, Proost P E A, Ongel Z, van Assouw H P & Gilissen R A H J (2003). Simultaneous measurement of drug metabolic stability and identification of metabolites using ion-trap mass spectrometry. Rapid Commun Mass Sprectrom, vol 17, 2661-2668), and the %-compound metabolised was calculated by the following equation:

%-compound metababolised=100%−%-compound remaining.

The results are shown in Table 4.

TABLE 4

%-compound metabolised using human liver microsomes (hLM), mouse liver microsomes (mLM) and guinea pig microsomes (gpLM)

| Co. No. | %-compound metabolised_Met_hLM | %-compound metabolised Met_mLM | %-compound metabolised Met_gpLM |
|---|---|---|---|
| 5 | 59 | 72 | 88 |
| 17 | 50 | 70 | 84 |
| 26 | 19 | 45 | 44 |
| 21 | 17 | 24 | 64 |
| 22 | 27 | 37 | 73 |
| 16 | 87 | 97 | 100 |
| 25 | 80 | n.d. | n.d. |
| 13 | 69 | n.d. | 95 |
| 23 | 22 | n.d. | 39 |
| 15 | 17 | n.d. | 44 |
| 19 | 36 | n.d. | 80 |
| 18 | 17 | n.d. | 36 |
| 24 | 20 | n.d. | 53 |
| 20 | 26 | n.d. | 88 |
| 28 | 2 | 41 | 21 |
| 1 | 43 | 51 | 86 |

Example D.3

Plasma Protein Binding Assay

Plasma was freshly prepared by centrifugation of guinea pig blood for 10 min at 1900 g in K3-EDTA (Ethylenediaminetetraacetic acid) coated tubes. The plasma protein binding of compounds was assessed at 5 µM concentrations as described by Van Liemp et al. 2010 (Van Liemp S, Morrison D, Sysmans L, Nelis P & Mortishire-Smith R (2010). Development and Validation of a Higher-Throughput Equilibrium Dialysis Assay for Plasma Protein Binding. Journal of the Association for Laboratory Automation, 2010, in press) using a rapid equilibrium device (RED). Briefly, guinea pig plasma was mixed with 5 µM test compound and then applied to the RED. Equilibrium was achieved after 4 h incubation at 37° C. Compound concentrations in the buffer and plasma compartment of the device were measured by LC-MS/MS.

For compound 15, the fraction bound was 98.48%.

Example D.4

Cytochrome P450 Inhibition Assays

Protocol A: Cytochrome P450 Results (% Inhibition) Using cDNA Expressed Proteins.

All fluorogenic based assays were performed in Black Costar 96-well plates according to Crespi et al 1997 with minor modifications (Crespi C L, Miller V P & Penman B W (1997). Microtiter plate assays for inhibition of human, drug-metabolizing cytochromes P450. Anal. Biochem. Vol 248, 1898-1900). Assay conditions are outlined in Table 5a. For cytochrome P450 3A4, three different fluorogenic substrates were used. Each reaction mixture consisted of the appropriate concentration of enzyme, NADPH-generating system ("NADPH" means β-nicotinamide adenine dinucleotide phosphate, reduced), substrate in sodium/potassium buffer (pH 7.4). For each cytochrome P450 batch Michealis-Menten kinetics were determined using 11 concentrations.

To determine $IC_{50}$ values or %-inhibition at 10 µM with the fluorogenic substrates, inhibitor stock solutions of 5 mM were made in dimethylsulfoxide (DMSO). Thereafter, further dilutions were made in acetonitrile. The final organic solvent concentration was, causing less than 10% inhibition, 2% (v/v). The compounds were serially diluted to give final concentrations ranging from 1 nM to 10 µM. The reaction mixtures, whereby 1 µL of buffer was replaced by compound solution, were pre-warmed for 5 min at 37° C. and the reaction was initiated by the addition of β-nicotinamide adenine dinucleotide phosphate (NADP+). Reactions were terminated by addition of stopping reagent and the fluorescence was measured using a Fluoroscan (Labsystems, Brussel, Belgium).

TABLE 5a

Cytochrome P450 inhibition assay conditions

| Condition | CYP1A2 | CYP2C9 | CYP2D6 | CYP3A4 |
|---|---|---|---|---|
| Enzyme Amount (pmol P450/ml) | 5 | 60 | 42 | 84/20/5 |
| Incubation Time (min) | 15 | 30 | 45 | 30/30/10 |
| Substrate | CEC | MFC | AMMC | BFC/BQ/DBF |
| Substrate concentration (µM) | 5 | 10 | 3 | 150/150/150 |
| Excitation (nm) | 410 | 405 | 405 | 405/405/485 |
| Emission (nm) | 460 | 535 | 460 | 535/535/535 |

In Table 5a, the following abbreviations were used: 3-cyano-7-ethocycoumarin (CEC), 7-methoxy-4-trifluoromethylcoumarin (MFC), 3-[2-(N,N-diethyl-N-methylamino)ethyl]-7-methoxy-4-methylcoumarin (AMMC), 7-benzyloxy-trifluoromethyl coumarin (BFC), 7-benzyloxyquinoline (BQ) and dibenzyl fluorescein (DBF).

TABLE 5b shows the Cytochrome P450 results (% inhibition) using cDNA expressed proteins at 10 µM

| Co. No. | hCYP3A4_BFC_Pct_Inh | hCYP3A4_BQ_Pct_Inh | hCYP3A4_DBF_Pct_Inh |
|---|---|---|---|
| 26 | 33 | 32 | 55 |
| 21 | 0 | 26 | 26 |
| 22 | 39 | 63 | 89 |
| 16 | 29 | 46 | 64 |

TABLE 5b-continued shows the Cytochrome P450 results (% inhibition) using cDNA expressed proteins at 10 μM

| | | | |
|---|---|---|---|
| 25 | 21 | 29 | 21 |
| 13 | 81 | 78 | 91 |
| 23 | 51 | 56 | 40 |
| 15 | 1 | 40 | 16 |
| 19 | 26 | 49 | 49 |
| 24 | 3 | 39 | 3 |
| 20 | 1 | 25 | 5 |

| Co. No. | hCYP2C9_MFC_Pct_Inh | hCYP2D6_AMMC_Pct_Inh | hCYP1A2_CEC_Pct_Inh |
|---|---|---|---|
| 26 | 69 | 74 | 34 |
| 21 | 54 | 39 | 27 |
| 22 | 85 | 53 | 20 |
| 16 | 84 | 55 | 55 |
| 25 | 45 | 11 | 21 |
| 13 | 61 | 51 | 64 |
| 23 | 51 | 3 | 17 |
| 15 | 60 | 63 | 38 |
| 19 | 60 | 33 | 44 |
| 24 | 54 | 3 | 18 |
| 20 | 43 | 20 | 18 |

TABLE 5c

Cytochrome P450 results (% inhibition) using cDNA expressed protein at 10 μM—present application vs. prior art

| hCYP3A4_BFC_Pct_Inh | hCYP3A4_BQ_Pct_Inh | hCYP3A4_DBF_Pct_Inh | hCYP2C9_MFC_Pct_Inh | hCYP2D6_AMMC_Pct_Inh | hCYP1A2_CEC_Pct_Inh |
|---|---|---|---|---|---|

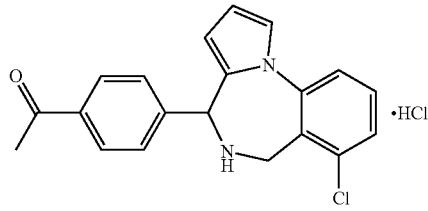

Compound 5 of the present application

| 57 | 57 | 70 | 54 | 53 | 12 |

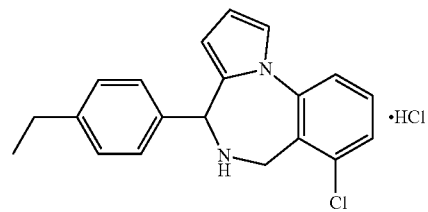

Hydrochloric acid salt of compound 2 of WO02/34752

| 64 | 57 | 69 | 68 | 96 | 48 |

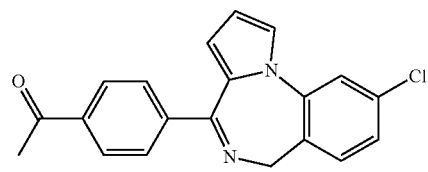

Compound 18 of the present application

| 7 | 50 | 40 | 69 | 20 | 21 |

TABLE 5c-continued

Cytochrome P450 results (% inhibition) using cDNA expressed protein at 10 μM—present application vs. prior art

| hCYP3A4_BFC_Pct_Inh | hCYP3A4_BQ_Pct_Inh | hCYP3A4_DBF_Pct_Inh | hCYP2C9_MFC_Pct_Inh | hCYP2D6_AMMC_Pct_Inh | hCYP1A2_CEC_Pct_Inh |
|---|---|---|---|---|---|
| | | Compound 23 of WO02/34752 | | | |
| 55 | 66 | 70 | 50 | 33 | 40 |
| | | Compound 17 of the present application | | | |
| 2 | 33 | 21 | 82 | 18 | 33 |
| | | Compound 22 of WO02/34752 | | | |
| 45 | 62 | 64 | 41 | 52 | 60 |
| | | Compound 28 of the present application | | | |
| 5 | 17 | 1 | 48 | 5 | 5 |

Protocol B: Human Liver Microsomal Cytochrome P450 Inhibition Assays.

The CYP450 inhibition potential was also determined for compound 18 using human liver microsomes against cytochrome 1A2 and 2D6.

Test compounds (TCs) were incubated across a concentration range (0 to 30 micromolar) with human liver microsomes and separate probe substrates ((resorufin for CYP1A2 and dextromethorphan for CYP2D6) to estimate the $IC_{50}$-value for inhibition of the probe substrate by the TC. TCs were dissolved in solvent condition A (0.15% DMSO+0.46% acetonitrile) or condition B (0.30% DMSO+0.68% acetonitrile). Assays were performed in 0.1 M phosphate buffer (pH 7.4), containing 1.0 mg/ml human liver microsomes (BD Gentest) and the probe substrate (either resorufin or dextromethorphan) and a range of test compound concentrations (0 to 30 micromolar) in a total volume of 250 microliters. After a 10 min pre-incubation at 37° C., the reaction was started with addition of NADPH at a final concentration of 1.0 mM. After an incubation of 10 min at 37° C. the reaction is quenched with 2 volumes of chilled DMSO. The samples are centrifuged for 10 min at 4° C. at 4000 rpm and the supernatant is analyzed. Analysis for CYP1A2 with resorufin was performed by fluorescence while the CY2D6 inhibition potential was assessed using LC-MS detection. No IC50 curves could be constructed to determine the IC50-values for Compound 18 since the %-inhibition for the two cytochrome P450s (1A2 and 2D6) was weak: For CYP1A2 using solvent condition A, the inhibition was 20-25% at 30 μM; and by using solvent condition B, the inhibition was 25-35% at 30 μM. For CYP2D6 using solvent condition B, the inhibition was 40-45% at 30 μM.

Protocol C: Human Liver Microsomal Cytochrome P450 Cocktail Inhibition Assay

Test compounds (TCs) were incubated across a concentration range (0 to 30 micromolar) with human liver microsomes and probe substrates for each of the six cytochrome P450s to estimate the $IC_{50}$-value for inhibition of the probe substrate by the TC.

Probe substrates and final assay concentrations with the appropriate internal standard are outlined in Table 6a.

Assays were performed in 0.1 M phosphate buffer (pH 7.4), containing 0.2 mg/ml human liver microsomes (BD Gentest) and a probe substrate mix consisting of: phenacetin, tolbutamide, S-mephenyloin, dextromethorphan, amodiaquine and midazolam (Table 6a) and a range of test compound concentrations (0 to 30 micromolar) in a total volume of 100 microliters. After a 10 min pre-incubation at 37° C., the reaction was started with addition of NADPH at a final concentration of 1.0 mM. The final organic solvent in the incubation is 0.15% DMSO and 0.8% acetonitrile. After an incubation of 10 min at 37° C. the reaction is quenched with 1.6 volumes of chilled quenching solution consisting of DMSO and the internal standards (Table 6a). The samples are centrifuged for 10 min at 4° C. at 4000 rpm and 60 microliters supernatant is diluted with 180 microliters water. Each sample is injected onto a UPLC/MS system for the simultaneous measurement of the probe substrate metabolites and their associated deuterated internal standards. Percentage inhibition is calculated according to:

%-inhibition=$(1-Ri/R)*100$, whereby $Ri$ and $R$ are the metabolite to internal standard peak area ratios in the presence and absence of inhibitor respectively.

Percentage inhibition data are plotted against the Log transformed test compound concentration and after curve fitting the $IC_{50}$-value is determined.

TABLE 6a

Probe substrate and internal standards for the Human liver microsomal P450 inhibition cocktail assay.

| Cytochrome P450 | Probe Substrate | Probe Substrate concentration (microM) | Internal Standard |
| --- | --- | --- | --- |
| 1A2 | Phenacetin | 80 | Acetaminophen-D4 |
| 2C8 | Amodiaquine | 2 | N-desethylamodiaquine-D4 |
| 2C9 | Tolbutamide | 100 | 4-hydroxytolbutamide-D9 |
| 2C19 | S-Mephenytoin | 30 | 4-hydroxymephenytoin-D3 |
| 2D6 | Dextromethorphan | 3 | Dextromethorphan-D3 |
| 3A4/5 | Midazolam | 2 | 1'-hydroxymidazolam-D4 |

TABLE 6b shows the $pIC_{50}$ values—present application vs. prior art

| 1A2_Phen | 2C8_Amod | 2C9 Tolbut | 2C19_S-Meph | 2D6_Dextro | 3A4_mido |
| --- | --- | --- | --- | --- | --- |

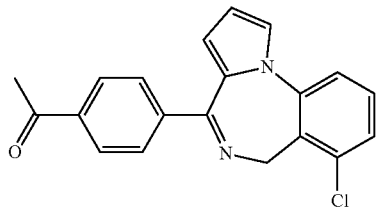

Compound 17 of the present application

| <5.0 | <5.0 | <5.0 | <5.0 | <5.0 | <5.0 |

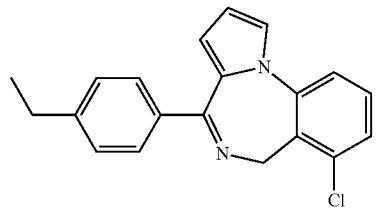

Compound 22 of WO02/34752

| <5.0 | <5.0 | <5.0 | 5.8 | <5.0 | <5.0 |

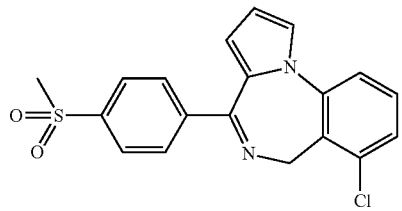

Compound 28 of the present application

| <5.0 | <5.0 | <5.0 | <5.0 | 5.12 | Not determined |

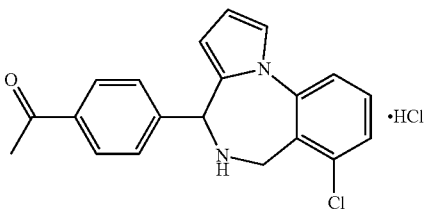

Compound 5 of the present application

| <5.0 | 5.1 | 5.5 | 5.5 | 5.5 | 5.1 |

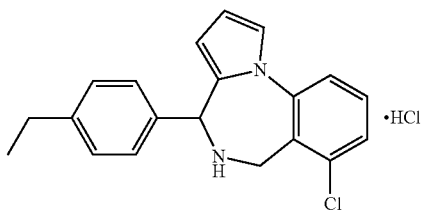

Hydrochloric acid salt of compound 2 of WO02/34752

| <5.0 | <5.0 | 5.0 | 6.0 | 5.5 | 5.2 |

TABLE 6b-continued shows the pIC$_{50}$ values—present application vs. prior art

| 1A2_Phen | 2C8_Amod | 2C9 Tolbut | 2C19_S- Meph | 2D6_Dextro | 3A4_mido |
|---|---|---|---|---|---|

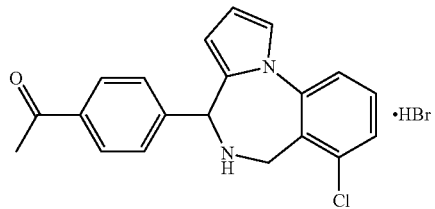

Compound 6 of the present application

| <5.0 | 5.1 | 5.6 | 5.9 | 5.7 | 5.3 |

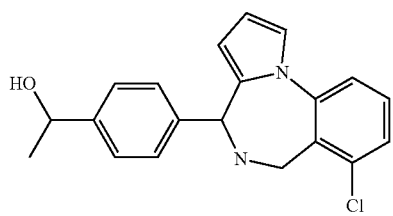

Compound 1 of the present application

| <5.0 | <5.0 | <5.0 | 5.29 | <5.0 | <5.0 |

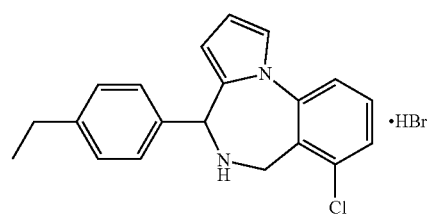

Compound 2 of WO02/34752

| <5.0 | <5.0 | 5.1 | 6.1 | 5.7 | <5.0 |

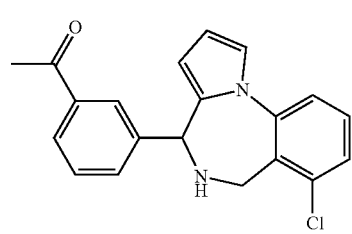

Compound 4 of the present application

| <5.0 | 5.1 | 5.8 | 6.8 | 5.5 | 5.6 |

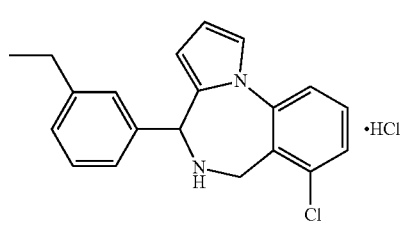

Compound 25 of WO02/34752

| <5.0 | <15.0 | 5.2 | 5.9 | 5.7 | 5.6 |

TABLE 6b-continued shows the pIC$_{50}$ values—present application vs. prior art

| 1A2_Phen | 2C8_Amod | 2C9 Tolbut | 2C19_S- Meph | 2D6_Dextro | 3A4_mido |
|---|---|---|---|---|---|

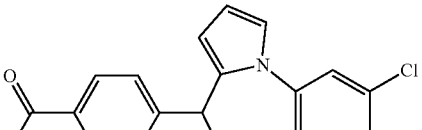

Compound 8 of the present application

| <5.0 | 5.1 | 5.2 | 5.5 | 5.1 | 5.0 |

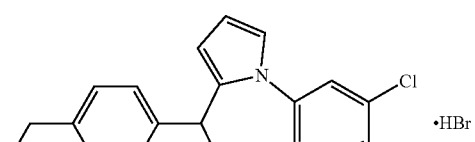

Compound 16 of WO02/34752

| <5.0 | <5.0 | 5.0 | 6.5 | 5.4 | 5.2 |

Example D.5

Calculated Log of the Octanol/Water Partition Coefficient (C log P)

The calculated log of the octanol/water partition coefficient was obtained by using Bio-Loom software (BioByte).

TABLE 7

| | ClogP |
|---|---|
| Compound (present application) | |
| 18 | 4.13 |
| 17 | 3.92 |
| 28 | 3.10 |
| 5 | 3.71 |
| 8 | 3.91 |
| 6 | 3.71 |
| 4 | 3.71 |
| 1 | 3.54 |
| Compound (prior art) | |
| 25 (WO02/34752) | 5.30 |
| 23 (WO02/34752) | 5.47 |
| 22 (WO02/34752) | 5.47 |
| 32 (WO02/34752) | 5.30 |
| 16 (WO02/34752) | 5.30 |
| 2 (WO02/34752) | 5.30 |
| HCl salt of compound 2 of WO02/34752 | 5.30 |

E. Composition Example

"Active ingredient" as used throughout these examples, relates to a compound of Formula (I), including any stereochemically isomeric form thereof, a pharmaceutically

Example E1

Injectable Solution 1.8 Grams methyl 4-hydroxybenzoate and 0.2 grams sodium hydroxide are dissolved in about 0.5 l of boiling water for injection. After cooling to about 50° C. there are added while stirring 0.05 grams propylene glycol and 4 grams of the active ingredient. The solution is cooled to room temperature and supplemented with water for injection q.s. ad 1 l, giving a solution comprising 4 mg/ml of active ingredient. The solution is sterilized by filtration and filled in sterile containers.

Example E2

Transungual Composition 0.144 g $KH_2PO_4$, 9 g NaCl, 0.528 g $Na_2HPO_4.2H_2O$ is added to 800 ml $H_2O$ and the mixture is stirred. The pH is adjusted to 7.4 with NaOH and 500 mg $NaN_3$ is added. Ethanol (42 v/v %) is added and the pH is adjusted to 2.3 with HCl.

15 mg active ingredient is added to 2.25 ml PBS (Phosphate Buffer Saline)/Ethanol (42%; pH 2.3) and the mixture is stirred and treated with ultrasound. 0.25 ml PBS/Ethanol (42%; pH 2.3) is added and the mixture is further stirred and treated with ultrasound until all active ingredient is dissolved, yielding the desired transungual composition.

Example E3

Oral Drops

500 Grams of the A.I. is dissolved in 0.5 l of a sodium hydroxide solution and 1.5 l of the polyethylene glycol at 60~80° C. After cooling to 30~40° C. there is added 35 l of polyethylene glycol and the mixture is stirred well. Then there is added a solution of 1750 grams of sodium saccharin in 2.5 l of purified water and while stirring there are added 2.5 l of cocoa flavor and polyethylene glycol q.s. to a volume of 50 l, providing an oral drop solution comprising 10 mg/ml of A.I. The resulting solution is filled into suitable containers.

Example E4

Capsules

20 Grams of the A.I., 6 grams sodium lauryl sulfate, 56 grams starch, 56 grams lactose, 0.8 grams colloidal silicon dioxide, and 1.2 grams magnesium stearate are vigorously stirred together. The resulting mixture is subsequently filled into 1000 suitable hardened gelatin capsules, comprising each 20 mg of the active ingredient.

Example E5

Film-Coated Tablets

Preparation of Tablet Core

A mixture of 100 grams of the A.I., 570 grams lactose and 200 grams starch is mixed well and thereafter humidified with a solution of 5 grams sodium dodecyl sulfate and 10 grams polyvinylpyrrolidone in about 200 ml of water. The wet powder mixture is sieved, dried and sieved again. Then there is added 100 grams microcrystalline cellulose and 15 grams hydrogenated vegetable oil. The whole is mixed well and compressed into tablets, giving 10.000 tablets, each containing 10 mg of the active ingredient.

Coating

To a solution of 10 grams methyl cellulose in 75 ml of denaturated ethanol there is added a solution of 5 grams of ethyl cellulose in 150 ml of dichloromethane. Then there are added 75 ml of dichloromethane and 2.5 ml 1,2,3-propanetriol. 10 Grams of polyethylene glycol is molten and dissolved in 75 ml of dichloromethane. The latter solution is added to the former and then there are added 2.5 grams of magnesium octadecanoate, 5 grams of polyvinylpyrrolidone and 30 ml of concentrated colour suspension and the whole is homogenated. The tablet cores are coated with the thus obtained mixture in a coating apparatus.

Example E6

2% Cream

Stearyl alcohol (75 mg), cetyl alcohol (20 mg), sorbitan monostearate (20 mg) and isopropyl myristate (10 mg) are introduced in a doublewall jacketed vessel and heated until the mixture has completely molten. This mixture is added to a seperately prepared mixture of purified water, propylene glycol (200 mg) and polysorbate 60 (15 mg) having a temperature of 70 to 75° C. while using a homogenizer for liquids. The resulting mixture is allowed to cool to below 25° C. while continuously mixing. A solution of A.I. (20 mg), polysorbate 80 (1 mg) and purified water q.s. ad 1 g and a solution of sodium sulfite anhydrous (2 mg) in purified water are next added to the emulsion while continuously mixing. The cream is homogenized and filled into suitable tubes.

Example E7

2% Cream

A mixture of A.I. (2 g), phosphatidyl choline (20 g), cholesterol (5 g) and ethyl alcohol (10 g) is stirred and heated at 55-60° C. until complete solution and is added to a solution of methyl paraben (0.2 g), propyl paraben (0.02 g), disodium edetate (0.15 g) and sodium chloride (0.3 g) in purified water (ad 100 g) while homogenizing. Hydroxypropylmethylcellulose (1.5 g) in purified water is added and the mixing is continued until swelling is complete.

The invention claimed is:
1. A compound of formula (I)

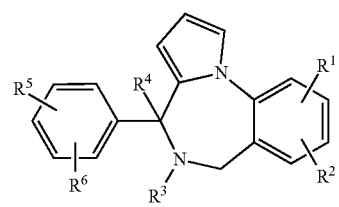

or a stereoisomeric form thereof, wherein
$R^1$ is hydrogen, halo, $C_{1-4}$alkyl or $C_{1-4}$alkyloxy;
$R^2$ is hydrogen or halo;
$R^3$ and $R^4$ are hydrogen;
or $R^3$ and $R^4$ taken together form a bond;

$R^5$ is $C_{1-4}$alkylcarbonyl, $C_{1-4}$alkylsulphonyl, $C_{1-4}$alkylsulphinyl, or $C_{1-4}$alkyl substituted with one hydroxyl moiety;

$R^6$ is hydrogen or halo;

or a pharmaceutically acceptable addition salt thereof.

2. The compound according to claim 1 wherein $R^1$ is hydrogen, halo, $C_{1-4}$alkyl or $C_{1-4}$alkyloxy;

$R^2$ is hydrogen or halo;

$R^3$ and $R^4$ are hydrogen;

or $R^3$ and $R^4$ taken together form a bond;

$R^5$ is $C_{1-4}$alkylcarbonyl; $C_{1-4}$alkylsulphonyl; or $C_{1-4}$alkyl substituted with one hydroxyl moiety;

$R^6$ is hydrogen or halo;

or a pharmaceutically acceptable addition salt thereof.

3. The compound according to claim 1 wherein $R^1$ is chloro or fluoro;

$R^2$ is hydrogen, chloro of fluoro;

$R^5$ is methylcarbonyl, methylsulphonyl or 1-hydroxyethyl;

$R^6$ is hydrogen or fluoro.

4. The compound according to claim 1 wherein $R^5$ is $C_{1-4}$alkylcarbonyl.

5. The compound according to claim 1 wherein $R^1$ is halo.

6. The compound according to claim 1 wherein the compound is a compound of formula (I-x) or (I-y)

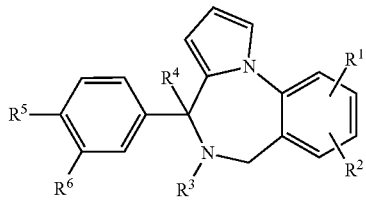

(I-x)

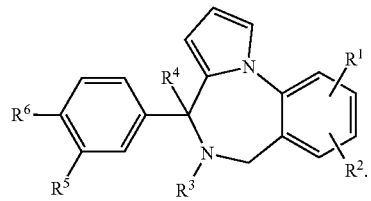

(I-y)

7. The compound according to any one of claims 1 to 6 wherein $R^3$ and $R^4$ are taken together to form a bond.

8. A pharmaceutical composition comprising a pharmaceutically acceptable carrier and, as active ingredient, a therapeutically effective amount of a compound as defined in claim 1.

9. A method of treating a patient with a fungal infection, said method comprising administering to said patient a therapeutically effective amount of a compound of claim 1.

10. The method according to claim 9 wherein the fungal infection is caused by one or more of the fungi selected from the group consisting of *Candida* spp.; *Aspergillus* spp.; *Cryptococcus neoformans*; *Sporothrix schenckii*; *Epidermophyton floccosum*; *Microsporum* spp.; *Trichophyton* spp; *Fusarium* spp.; *Rhizomucor* spp.; *Mucor circinelloides*; *Rhizopus* spp.; *Malassezia furfur*; *Acremonium* spp.; *Paecilomyces*; *Scopulariopsis*; *Arthrographis* spp.; *Scytalidium*; *Scedosporium* spp.; *Trichoderma* spp.; *Penicillium* spp.; *Penicillium marneffei*; *Blastoschizomyces*.

11. The method according to claim 9 wherein the fungal infection is caused by one or more of the fungi selected from the group consisting of *Candida parapsilosis*; *Aspergillus* spp.; *Cryptococcus neoformans*; *Sporothrix schenckii*; *Epidermophyton floccosum*; *Microsporum* spp.; *Trichophyton* spp.; *Fusarium* spp.; *Rhizomucor* spp.; *Mucor circinelloides*; *Rhizopus* spp.; *Acremonium* spp.; *Paecilomyces*; *Scopulariopsis*; *Arthrographis* spp.; *Scytalidium*; *Scedosporium* spp.; *Trichoderma* spp.; *Penicillium* spp.; *Penicillium marneffei*; *Blastoschizomyces*.

12. The method according to claim 9 wherein the fungal infection is caused by one or more of the fungi selected from the group consisting of *Microsporum canis, Trichophyton mentagrophytes, Trichophyton rubrum* and *Aspergillus fumigatus*.

* * * * *